(12) United States Patent
Callas et al.

(10) Patent No.: US 10,130,819 B2
(45) Date of Patent: Nov. 20, 2018

(54) SYSTEM AND METHOD FOR SYNCHRONIZING ENERGY DELIVERY TO THE CARDIAC RHYTHM

(71) Applicant: AngioDynamics, Inc., Latham, NY (US)

(72) Inventors: Peter Callas, Castro Valley, CA (US); James Lovewell, San Leandro, CA (US); Bradley C. Stribling, Alamo, CA (US); Dave Warden, Belmont, CA (US)

(73) Assignee: AngioDynamics, Inc., Latham, NY (US)

(*) Notice: Subject to any disclaimer, the term of this patent is extended or adjusted under 35 U.S.C. 154(b) by 0 days.

(21) Appl. No.: 15/680,381

(22) Filed: Aug. 18, 2017

(65) Prior Publication Data

US 2017/0340888 A1 Nov. 30, 2017

Related U.S. Application Data

(63) Continuation of application No. 14/529,811, filed on Oct. 31, 2014, now Pat. No. 9,764,145, which is a continuation of application No. 12/790,681, filed on May 28, 2010, now Pat. No. 8,903,488.

(60) Provisional application No. 61/181,727, filed on May 28, 2009.

(51) Int. Cl.
*A61B 5/00* (2006.01)
*A61N 1/37* (2006.01)
*A61N 1/365* (2006.01)
*A61N 1/32* (2006.01)

(52) U.S. Cl.
CPC ........... *A61N 1/3706* (2013.01); *A61N 1/365* (2013.01); *A61N 1/3702* (2013.01); *A61N 1/327* (2013.01)

(58) Field of Classification Search
CPC .................................................. A61N 1/3706
USPC ........................................................... 607/9
See application file for complete search history.

*Primary Examiner* — Nadia A Mahmood
(74) *Attorney, Agent, or Firm* — Zachary F Madonna

(57) ABSTRACT

A system for synchronizing application of treatment signals with a cardiac rhythm is provided. The system includes a memory that receives and stores a synchronization signal indicating that a predetermined phase such as R-wave of a cardiac rhythm of a patient has started. A synchronization module analyzes whether the stored synchronization signal is erroneous and if so, prevents a medical treatment device from applying a treatment energy signal such as an IRE pulse to a patient to take into account an irregular heart beat and noise in the synchronization signal in order to maximize safety of the patient.

7 Claims, 22 Drawing Sheets

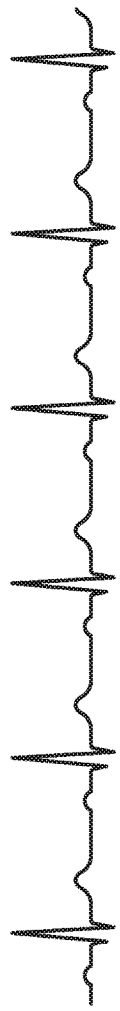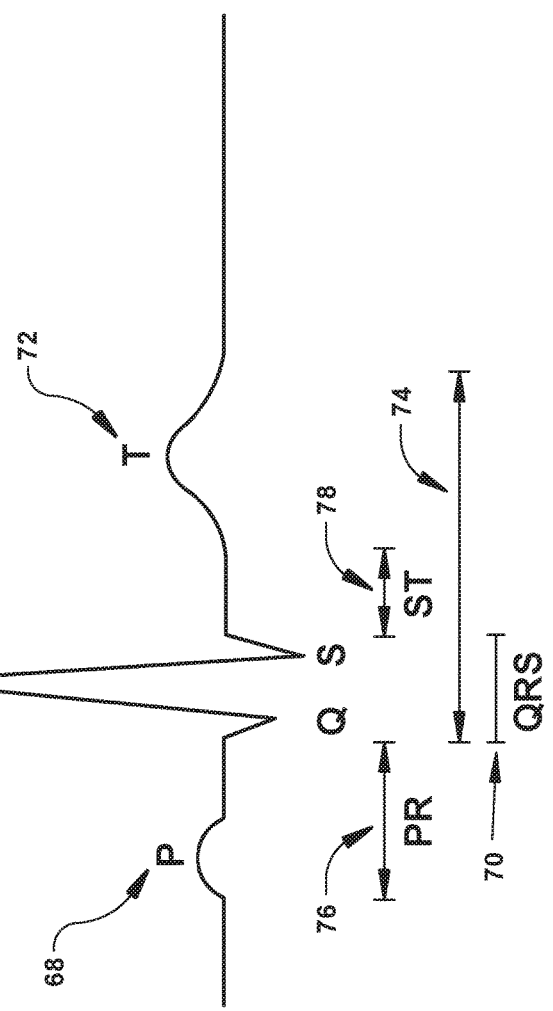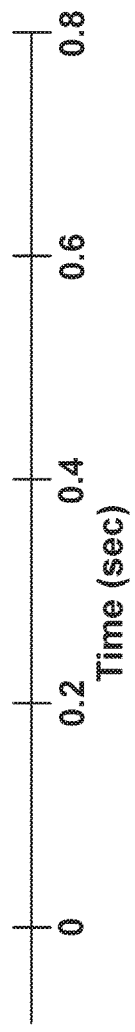
FIG. 4A
FIG. 4B
FIG. 4C

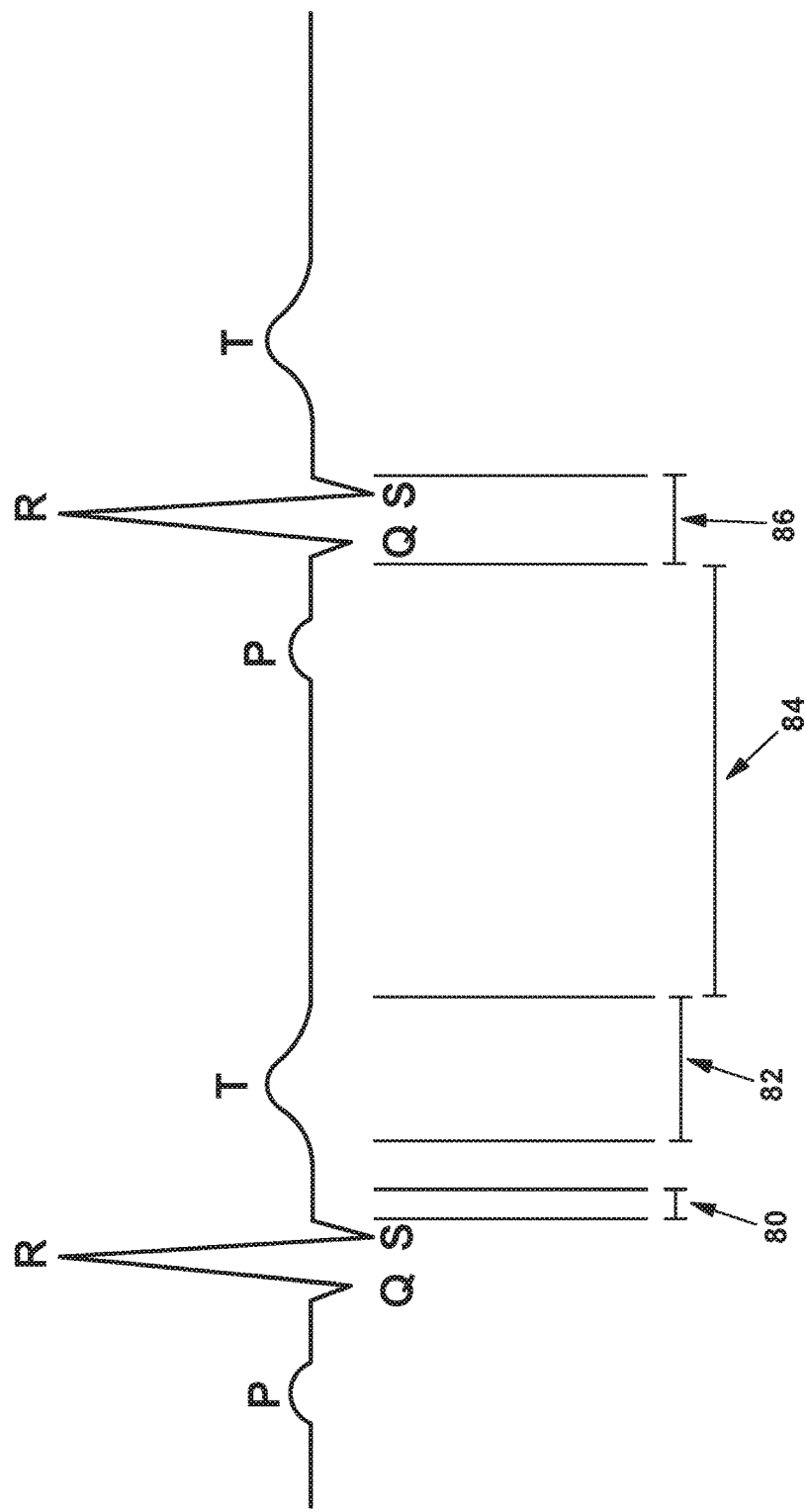

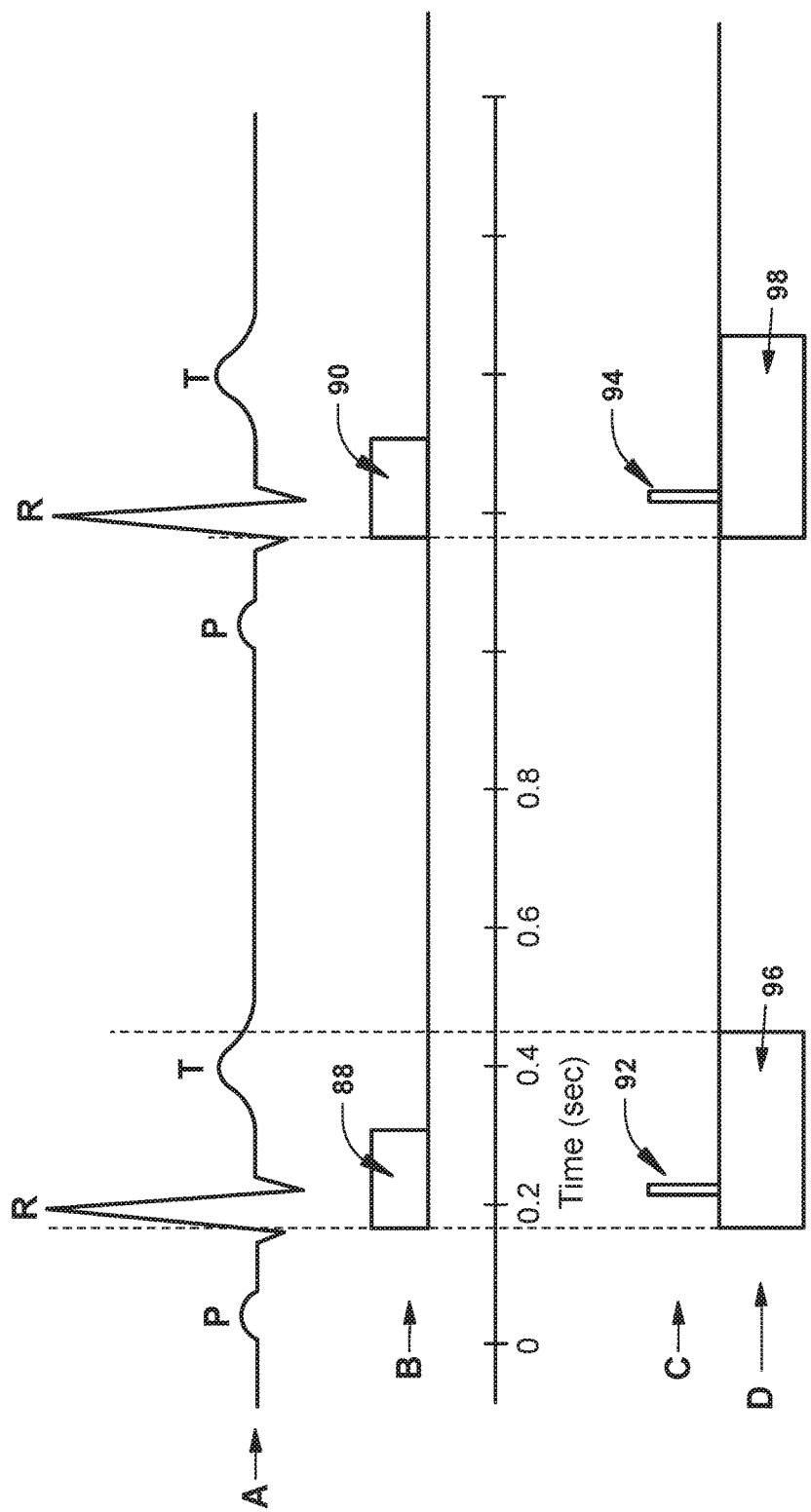

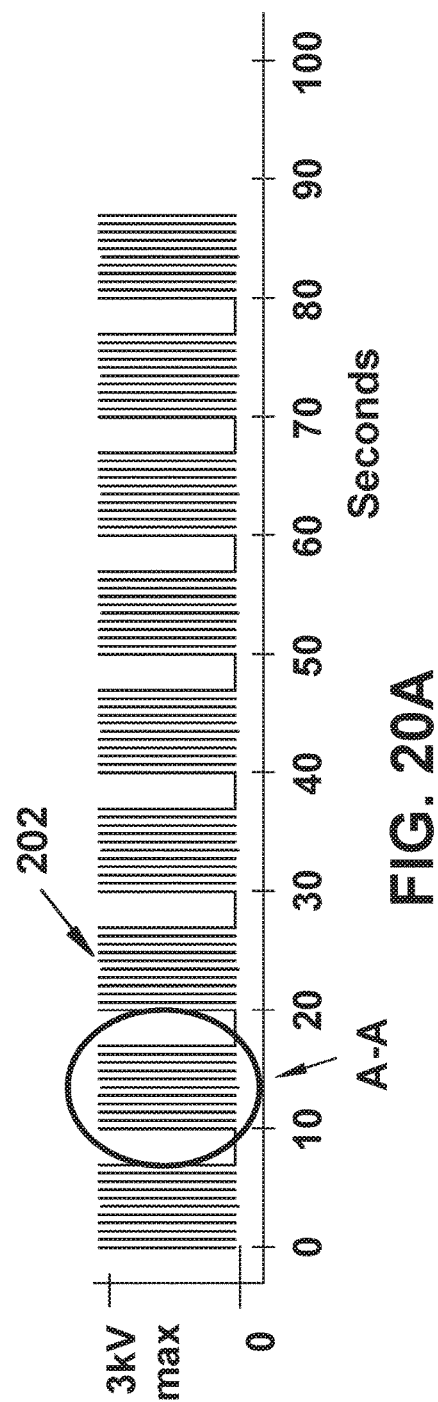
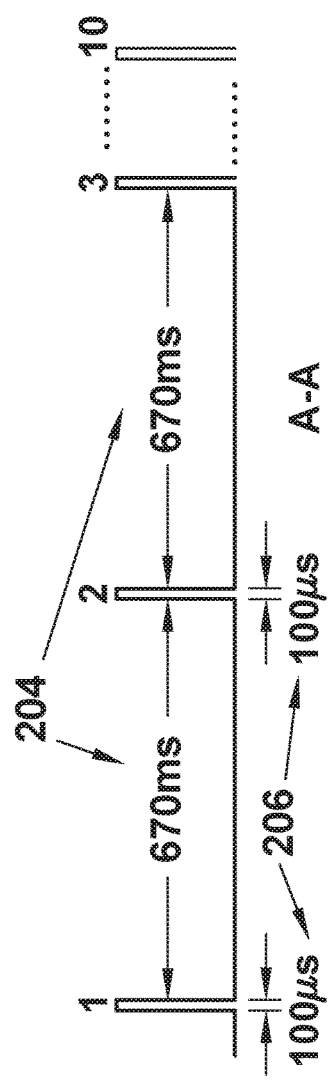
FIG. 20A
FIG. 20B

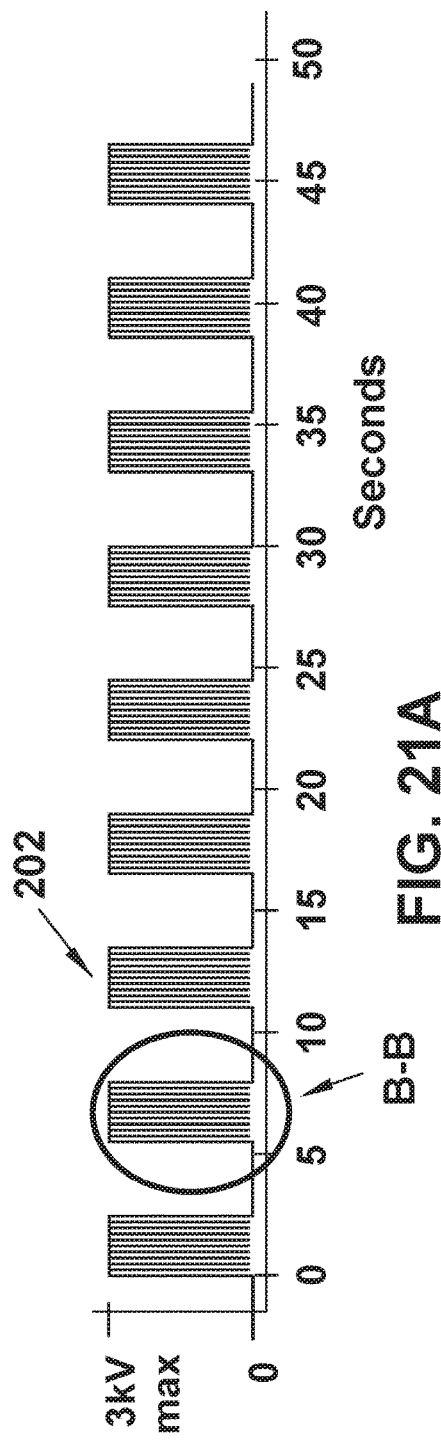
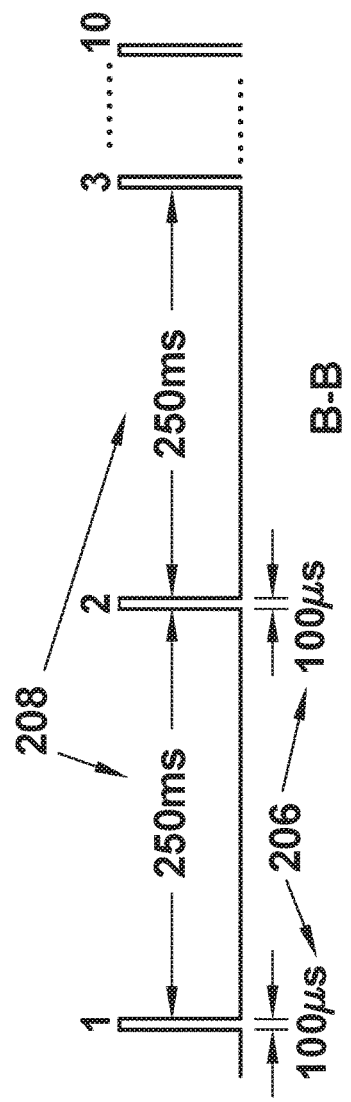
FIG. 21A
FIG. 21B

SYSTEM AND METHOD FOR SYNCHRONIZING ENERGY DELIVERY TO THE CARDIAC RHYTHM

CROSS REFERENCE TO RELATED APPLICATIONS

This application claims priority under 35 U.S.C. 119(e) to U.S. Provisional Application No. 61/181,727, filed May 28, 2009, which is incorporated herein by reference.

FIELD OF THE INVENTION

The present invention relates generally to a medical treatment device. More specifically, this present invention is related to system and method for synchronizing treatment signals with a cardiac cycle.

DESCRIPTION OF THE RELATED ART

Medical devices such as those for applying reversible electroporation (RE) or irreversible electroporation (IRE) pulses are used for patient treatments, therapies, and tissue ablation with great success. As these devices generate very high voltage treatment signals of up to several thousand volts, there is a possibility that it may interfere with normal heart functions if the treatment signals are applied at the wrong time. Possible interferences may include inducing atrial and ventricular flutter and fibrillation and premature heartbeats.

To avoid such interferences, these medical treatment devices are starting to be used with synchronization devices that apply treatment pulse signals at one or more predetermined phases of the cardiac cycle such as during the refractory period of the cardiac cycle which is the period after the ventricular contraction during which both the atria and the ventricles are at rest.

The synchronization devices are usually based on an electrocardiogram (ECG) signal. However, the synchronization devices often cannot precisely determine the predetermined phase because 1) the heartbeats can become irregular; 2) the treatment signals themselves may cause the ECG signal to be altered; 3) the ECG signal may become noisy due to improper ECG lead placements and interferences from other medical devices in an operating room.

Therefore, there is a need for an improved and safer system and method for synchronizing treatment energy signals with the cardiac rhythm.

SUMMARY OF THE DISCLOSURE

According to one aspect of the present invention, a system for synchronizing application of treatment signals with a cardiac rhythm is provided. The system includes a memory and a synchronization module. The memory receives and stores a synchronization signal indicating that a predetermined phase such as R-wave of a cardiac rhythm of a patient has started. The synchronization module analyzes whether the stored synchronization signal is erroneous and if so, prevents a medical treatment device from applying a treatment energy signal such as an IRE pulse to a patient to take into account an irregular heart beat and noise in the synchronization signal in order to maximize safety of the patient.

According to another aspect of the present invention, a method of synchronizing application of treatment signals with a cardiac rhythm is provided. A synchronization signal, which indicates that a predetermined phase of a cardiac rhythm of a patient has started, is continuously received. The received synchronization signal is analyzed to determine whether it is erroneous. If so, a medical treatment device is prevented from applying a treatment energy signal, which is potentially harmful to the heart, to the patient to ensure safety of the patient.

BRIEF DESCRIPTION OF THE DRAWINGS

A more complete understanding of the present invention may be derived by referring to the detailed description when considered in connection with the following illustrative figures. In the figures, like reference numbers refer to like elements or acts throughout the figures.

FIGS. 4A, 4B and 4C depict an ECG waveform for a healthy adult.

FIG. 5 shows a waveform of the ECG in relation to when energy should be released for treatment.

FIG. 6 shows a waveform of a normal cardiac rhythm and how the IRE pulse is released in accordance with a certain portion of that cardiac rhythm.

FIGS. 20A-B show a chart and expanded view of indicating a specific mode (mode 2) of IRE energy pulse delivery contemplated for the current invention.

FIGS. 21A-B show a chart and expanded view indicating a specific mode (mode 3) of IRE energy pulse delivery contemplated for the current invention.

Figure 1:
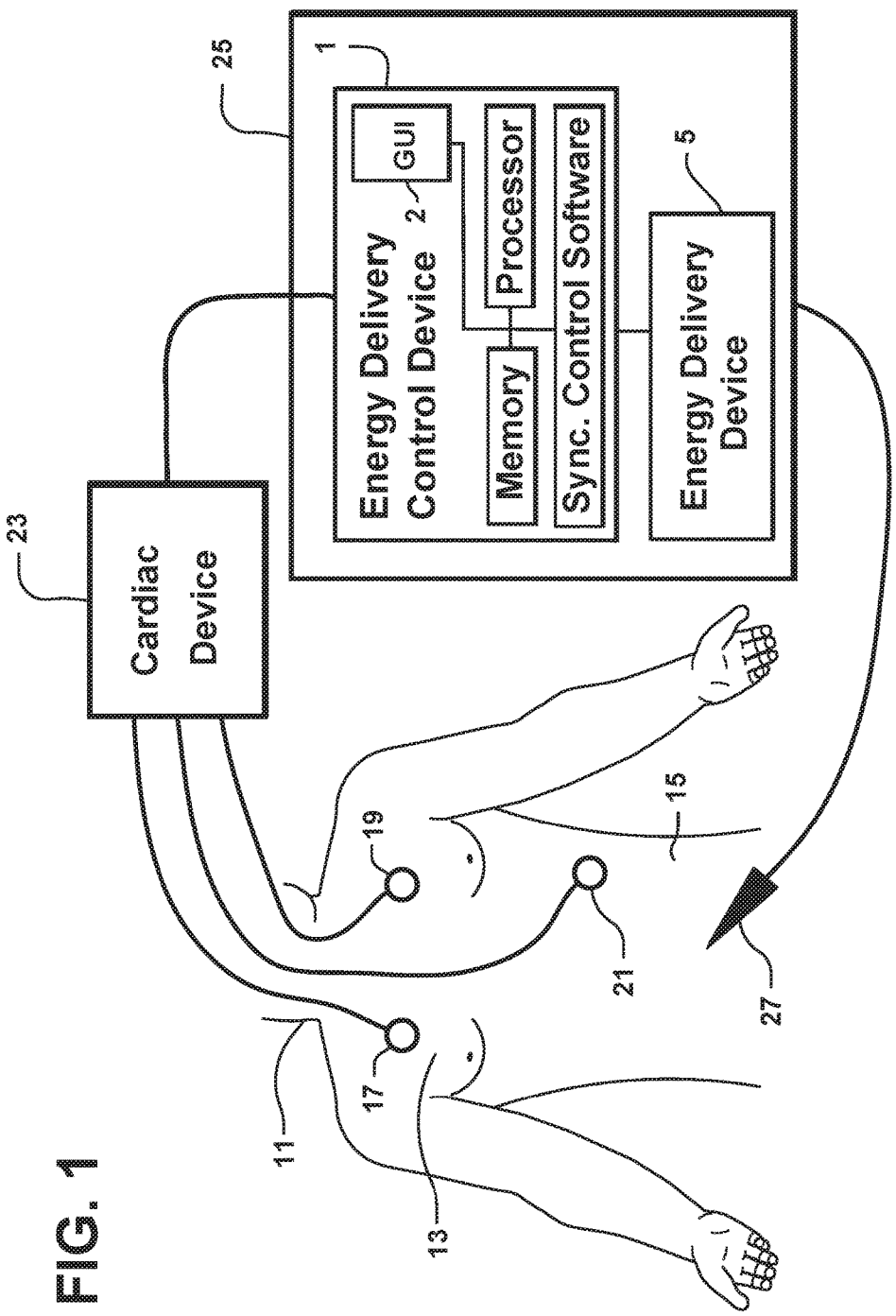
FIG. 1 depicts a treatment setup for a patient for synchronization of IRE pulse delivery with a specific portion of the cardiac rhythm.

Elements and acts in the figures are illustrated for simplicity and have not necessarily been rendered according to any particular sequence or embodiment.

DETAILED DESCRIPTION OF THE INVENTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention. It should be noted that there are many different and alternative configurations, devices and technologies to which the disclosed inventions may be applied. The full scope of the inventions is not limited to the examples that are described below.

The present invention provides a system and method involving a pulse delivery computer that will provide for application of treatment energy signals (such as IRE pulses) at specific times in the cardiac cycle such that patient safety is optimized. Herein, cardiac cycle refers to the repeatable phases of the heart such that energy release can be synchronized with specific points of those phases. It is recognized that there are mechanical and electrical aspects of the cycle, and the invention contemplates synchronization with any of the mechanical or electrical, repeatable phases of the heart. For clarity, the present invention will some times be explained in terms of delivering IRE pulses as a treatment energy signal.

The synchronization of cardiac rhythm with energy output may involve the use of medical treatment devices to release energy that can be used to ablate tissue. One example of such devices involves irreversible electroporation (IRE) technology, which is a novel methodology for ablating undesirable tissues such as cancer tissues. However, application of treatment energy signal such as IRE treatment signals to a patient potentially leads to adverse effects on cardiac function because the IRE treatment signals often involve electrical pulses of very high voltage, typically on the order of thousands of volts or more. Such high voltage pulses may potentially disrupt the cardiac rhythm. Disruption of the cardiac rhythm can lead to arrhythmias that can have dire medical consequences. The current invention provides for a energy delivery control device to release energy pulses using a flexible system that recognizes the state of the cardiac rhythm and reacts appropriately so as to provide energy release safely in a fashion currently unavailable.

As discussed above, one medical treatment device that can be used with the synchronization of cardiac rhythm is a device for applying IRE treatment signals. If properly designed, IRE is a technology that has the distinct advantage of inducing cell necrosis without causing thermal damage of tissue in the ablation zone. More specifically IRE is a technology where electrical pulses in the range of microseconds to milliseconds are applied to tissue to produce cellular necrosis and irreversible cell membrane permeabilization. IRE acts by creating defects in the cell membrane that lead to a disruption of homeostasis while sparing connective and scaffolding structure and tissue. These points have been addressed in the following publications, which are hereby incorporated by reference: Lavee J. *A Novel Nonthermal Energy Source for Surgical Epicardial Atrial Ablation: Irreversible Electroporation*. The Heart Surgery Forum. Vol. 10(2):96-101 (2007), and U.S. Patent Application Publication Number US 20060293731 A1, "Methods and systems for treating tumors using electroporation," application Ser. No. 11/165,961 filed on Jun. 24, 2005.

A distinct advantage of the IRE technology is the sparing of surrounding tissue, and in fact the structure of surrounding bile ducts, blood vessels, and connective tissue remains intact following application of IRE. This technology has been described in the following two patent application publications which are hereby incorporated by reference: Patent Application Publication Number WO2005/06284A2, "Tissue Ablation with Irreversible Electroporation," as well as U.S. Patent Application Publication Number US 2007/0043345A1, "Tissue Ablation with Irreversible Electroporation," application Ser. No. 10/571,162.

To optimize energy pulse delivery, the hardware and software relating to energy release in treatments and therapies involve coupling with a system to monitor cardiac rhythm, such as an electrocardiogram signal (ECG signal). This allows for release of energy at the proper time in a cardiac cycle. The ECG signal is used to diagnose cardiac arrhythmias through the recording and interpretation of the electrical activity of the cardiac cycle as recorded by an electrocardiograph which is a device generating the ECG signal.

The present invention can work with a wide variety of medical treatment devices and procedures. The invention can be used when the target tissue is one of the following tissues or is within the following tissues: digestive, skeletal, muscular, nervous, endocrine, circulatory, reproductive, integumentary, lymphatic, urinary, and soft tissue. The method and system can be used to target tissue of or within a vessel, a liver, or lung tissue. The method can also be used singly or in combination in tissues that are in the pancreas, prostate, uterus, and brain. The method can also be used to target singly or in combination tissues that are benign, malignant, cancerous, neoplastic, preneoplastic, dysplastic, tumorous or normal. In addition, the energy delivery control device can be used for safe and efficient treatments, therapies, and ablations for patients with normal cardiac rhythms, or acute or chronic irregularities as medically reasonable, including arrhythmias, sinus arrhythmia, sinus tachycardia, sick sinus syndrome, bradycardias, premature atrial contraction (PAC), supraventricular tachycardia (SVT), Wolff-Parkinson-White syndrome, atrial flutter, atrial fibrillation, premature ventricular complexes (PVC), ventricular tachycardia (VT), ventricular fibrillation, cardiac standstill (Asystole), and various heart blocks, as well as aberrations of the atrioventricular node, the sinoatrial node, and conduction irregularities.

As background, and to establish the state of the art in certain areas of technology, applicants herein expressly incorporate by reference all of the following materials identified below in numbered paragraphs.

Mali B., Jarm T, Corovic S, Paulin-Kosir M, Cemazar M, Sersa G, Miklavic D., *The effect of electroporation pulses on functioning of the heart*. Vol. 46(8): 745-757 (2008).

Fogoros R., *Electrophysiologic Testing*, $3^{rd}$ ed.; Blackwell Publishing, (1999).

Klabunde R, *Cardiovascular Physiology Concepts*; Lippincott Williams & Wilkins (2005).

In an example embodiment, the synchronization module maintains two indicators: a synchronization problem indicator and a synchronization condition indicator. When the synchronization problem indicator is set to logic zero, this is a representation of a normal operation, and when the synchronization problem indicator is set to logic one, this is an indication that a synchronization problem (error) exists. The synchronization problem indicator is used by the synchronization module to determine whether to allow delivery of a treatment energy signal/pulse to the patient as will be explained in detail later herein.

In the synchronization condition indicator, a setting of zero (logic state) means that too few synchronization signals (such as when an ECG lead is no longer in contact with the patient) are being received while when the synchronization condition indicator is set to logic one, this represents in this embodiment that too many synchronization signals (such as a heart rate over 120 beats per minute or in a noisy environment) are being received. Unlike the synchronization problem indicator, the synchronization condition indicator is not used in determining whether to deliver the treatment energy signals. They are only used by the GUI to display the condition of the synchronization if the synchronization problem indicator is set to high. For example, if the synchronization problem indicator is set to high and the synchronization condition indicator is set to low, the GUI may display a message that it is receiving too few signals and that it may be caused by the ECG leads being detached from the patient; on the other hand, if the synchronization problem indicator is set to high and the synchronization condition indicator is also set to high, the GUI may display a message that it is receiving too many synchronization signals which may indicate a very fast heart rate and that it may be caused by the patient under treatment.

FIG. 1 depicts a treatment setup for a patient for synchronization of energy pulse delivery with a specific portion of the cardiac rhythm. Shown is a patient with indicated neck 11, chest 13, and stomach 15 regions for perspective, along with electrocardiogram leads 17, 19, 21, a cardiac device 23 such as an electrocardiograph, and a treatment system 25 that can include an energy delivery control device 1 for synchronizing application of treatment signals with a cardiac rhythm, a graphic user interface (GUI) 2, which can be a part of the energy delivery control device and an energy delivery device 5 such as an IRE pulse generator that generates IRE treatment signals. The cardiac device 23 may be Accusync 72 ECG Trigger Monitor made by AccuSync Medical Research Corporation of Milford, Conn. Although shown for illustration purposes as a single device, the energy delivery control device 1 can comprise a synchronization control device such as Spartan-3 FPGA board with USB 2.0 made by CESYS GmbH of Germany, and a separate treatment planning computer coupled to the synchronization control device, both of which work with the GUI 2 to plan and control all aspects of a medical treatment procedure. In either case, the energy delivery control device 1 may include a memory for storing various parameters including synchronization signals from the cardiac device 23, blanking periods and various synchronization flags, a processor such as a CPU, synchronization software to be executed by the processor, and programmed logic downloaded into FPGA all working together to control the application of treatment energy signals into a patient. The memory, processor, GUI interface and sync control software are all connected to each other, for example, through a common bus. The term "synchronization module" is used herein to refer to either software or hardware or both which are required to analyze the synchronization signal and control the application of treatment energy signal based on such analysis. In one embodiment, the synchronization module comprises synchronization software and FPGA circuits that loads the software for execution. In another embodiment, the synchronization module comprises the synchronization control software and a processor as shown in FIG. 1. In one embodiment, the energy delivery device 5 comprises a high voltage pulse generator. Also shown is a set of electrodes 27 for pulse delivery to a part of the patient 15. The electrocardiograph can be a device involving one or more mechanical or electrical aspects that can include one or more computers. The output of the electrocardiograph can be on paper or digital display and can be based on a mechanical or electrical aspect or change in the heart.

Figure 2:
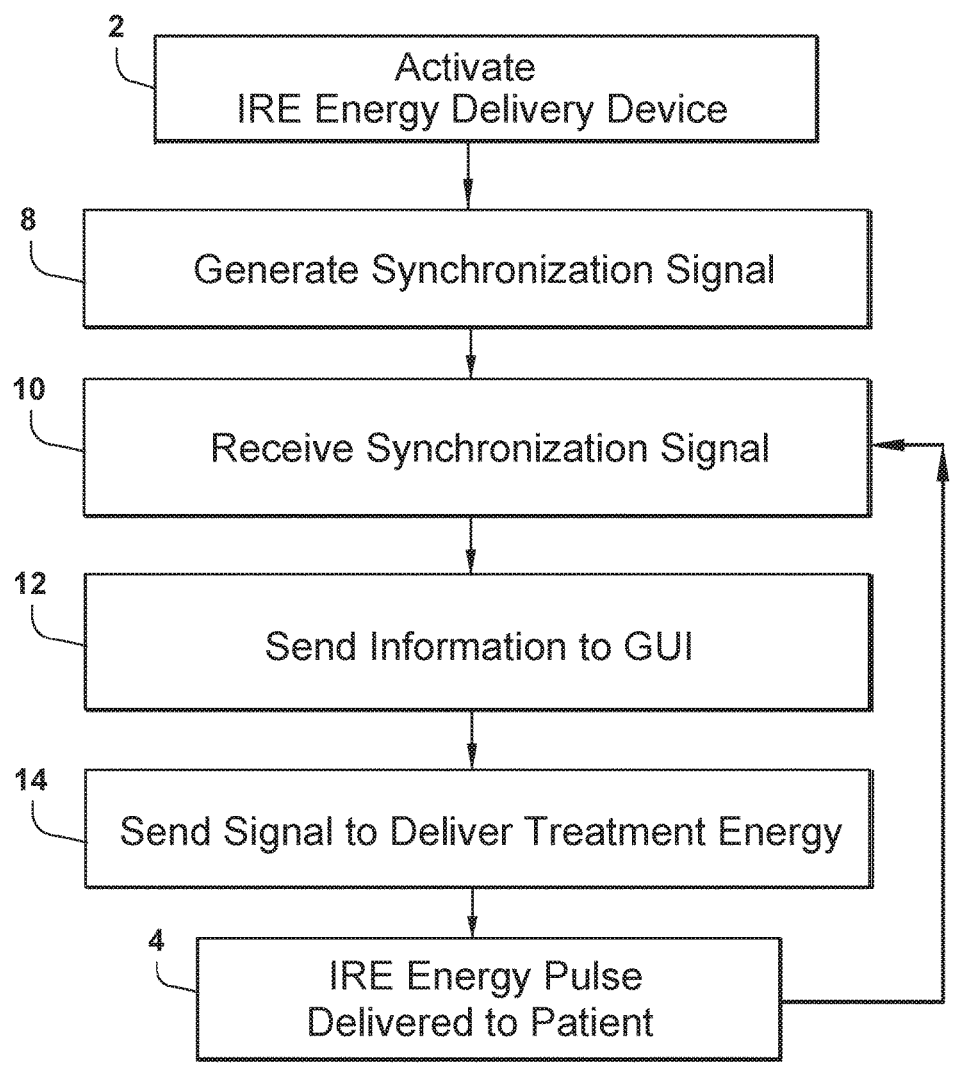
FIG. 2 depicts a flowchart showing a system for energy release to tissue of a patient.

FIG. 2 depicts a flowchart showing detailed plans for a treatment system 25 for energy release to tissue of a patient. This demonstrates the coordination between the energy delivery device 5 that releases IRE treatment energy to tissue of a patient, the cardiac device 23 that records the ECG of a patient, recognizes a specific phase of the cardiac rhythm such as an R-wave of the heartbeat and generates a continuous synchronization signal (e.g., a logic high state) indicating that the specific phase (e.g., R-wave) has started, and the energy delivery control device 1 that will receive the synchronization signal and control the timing of releasing treatment energy signals by the energy delivery device 5 (for clarity, the S wave could be a possible time for delivery of an energy pulse, but due to the fact the S wave ends nebulously in some cases, the R wave is preferably used as an indicator to start the timing of energy release). The control device 1 coupled to the energy delivery device 5 also communicates status and updates to the graphic user interface (GUI) 2 of the IRE energy unit so that they can be displayed in a display device (not shown). In various embodiments, the GUI interface 2 can be used to change one or more parameters or any of the programming of the (or related to the) energy delivery control device 1.

More specifically, the energy delivery control device 1 allows for monitoring of heart signals so as to ensure that changes, maladies, and other alterations associated with the heartbeat are coordinated such that pulses from the energy delivery device 5 are released at the proper time, and that if the heartbeat is out of its normal rhythm, that the release of energy is either altered or aborted. As will be explained in more detail later herein, in one specific embodiment, the goals of the treatment system are: 1) delivery of a first treatment energy signal soon (e.g., 50 milliseconds) after detection of the synchronization signal indicating that an R-wave of a cardiac cycle has been started and prevention of any subsequent treatment energy signal during the same cardiac cycle; 2) prevention of any treatment energy signal during a T-wave of the cardiac cycle; 3) dynamically adjusting the blanking period to account for noisy synchronization signal during which no other treatment energy signal can be delivered to the patient; 4) identification of a synchronization problem and prevention of delivering further treatment energy signals for at least the first cardiac cycle after the synchronization has been re-established; 5) abort the treatment procedure if the synchronization problem lasts for more than a certain time (e.g., more than 12 seconds).

Referring to FIG. 2, an energy delivery device 5 is activated by a physician by, for example, pressing a foot pedal to start a treatment procedure (step 2). The cardiac device 23 receives ECG information, determines the cardiac cycle stage for the patient and generates a synchronization signal indicating that a certain phase of the cardiac cycle has started (step 8). In the embodiment shown, the synchronization signal indicates that an R-wave cycle has been reached. In step 10, the energy delivery control device 1 continuously receives from the cardiac device 23 the synchronization signal. In step 12, the control device 1 sends synchronization status information to the GUI interface, where the information is displayed for users. In step 14, the control device 1 sends a signal to the energy delivery device 5 to deliver a treatment energy pulse/signal to the tissue of the patient under certain circumstances, and in step 4, the energy delivery device delivers the treatment energy to the patient. In the embodiment shown, the treatment energy signal is a single IRE pulse although the signal can comprise a sequence of IRE pulses. If more than one pulse is to be delivered, they should be delivered preferably within about 60 milliseconds of the start of the synchronization signal. The steps of 10, 12 and 14 are explained in more detail below with reference to FIGS. 3A-3C which represent the steps executed by the synchronization module within the energy delivery control device 1.

The present invention provides a system that reacts to changes in a normal cardiac rhythm, such as tachycardia or bradycardia. These changes are recognized and accounted for in the treatment energy IRE pulse delivery such that the release is still coordinated with the correct portion of the cardiac cycle, despite the change in rhythm. One way to begin to address changes in cardiac rhythms for IRE treatment energy signal release would be to dynamically adjust a blanking period programmed into the energy delivery control device 5 during which the software will prevent a pulse delivery for a set time. For example, upon receiving a synchronization signal, the software will instruct the energy delivery device 5 to deliver a first treatment energy signal to the patient and at the same time start a blanking period during which no other treatment energy is delivered. If a new synchronization signal is received by the energy delivery control device 1 during that same blanking period, subsequent treatment energy signal would not be delivered because the new synchronization signal is recognized as an erroneous signal.

Figure 3A:
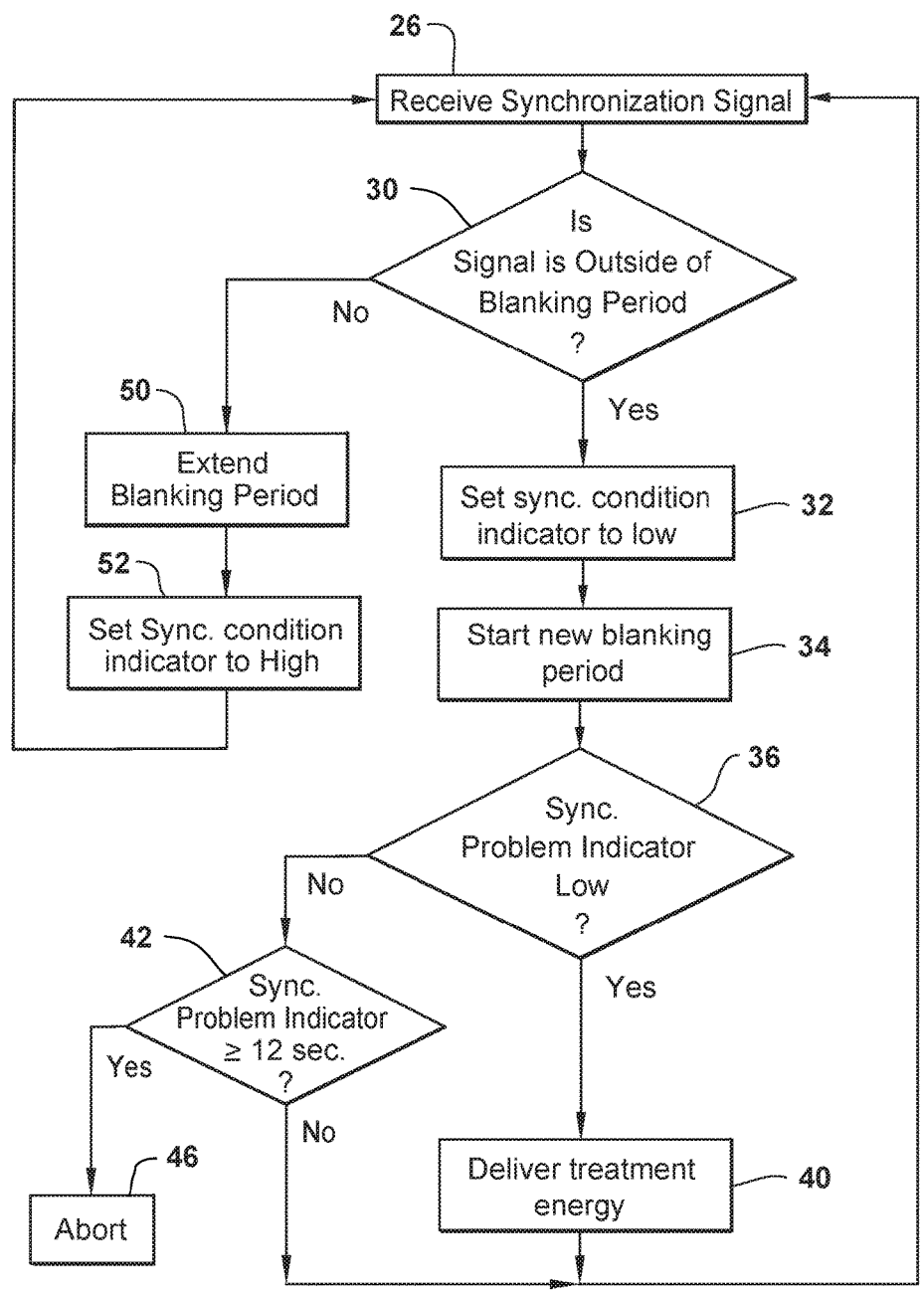
FIGS. 3A and 3B are flowcharts showing an energy delivery control device for synchronizing energy delivery to the cardiac rhythm according to the present invention.

Referring to FIG. 3A, in step 26, the energy delivery control device 1 monitors and receives the synchronization signal from the cardiac device 23. In the embodiment shown, the cardiac device 23 analyzes electrocardiogram information, determines the stage of the cardiac cycle 24 in real-time, and generates the synchronization signal indicating that a specific phase of the cardiac cycle has been reached. In the embodiment shown, the synchronization signal is a TTL signal which indicates that the R-wave phase has been reached (see exemplary synchronization signal 88 and 90 as depicted in FIG. 6). In step 30, the synchronization module determines whether the received synchronization signal is within or outside of the blanking period which would have been set up in the previous cardiac cycle.

In the embodiment shown, the blanking period is set to 500 milliseconds although the period can vary such as from 330 to 800 milliseconds so long as the period does not include the T-wave phase of the cycle.

In a normal cardiac rhythm and if the synchronization signal is being generated correctly, then the just received synchronization signal should be outside of the previously set blanking period. If so, step 32 is executed. In step 32, the synchronization condition indicator is set to low. As discussed above, the synchronization condition indicator does not affect the determination of whether to allow the delivery of a treatment energy signal.

In step 34, a new blanking period of 500 milliseconds is started since the received synchronization signal is assumed to be part of a new cardiac cycle. In step 36, the synchronization module determines whether the synchronization problem indicator is low.

If not, that means that the synchronization module has determined that there is a synchronization problem (e.g., the received synchronization signal is determined to be erroneous) and step 42 is executed. In step 42, the synchronization module determines whether the synchronization problem indicator has been set to high for 12 seconds or more. If so, the synchronization module considers the synchronization problem as unrecoverable and aborts the medical treatment procedure in step 46. If the synchronization problem indicator has been set to high for less than 12 seconds, that means the synchronization problem is considered to be recoverable. In that case, the synchronization module goes back to step 26 where it looks for another synchronization signal. It is important to note that by going back to step 26 to look for a new synchronization signal if the decision in step 42 is no, the just received synchronization signal is ignored and no treatment energy signal is delivered. Thus, if the system is just recovering from a synchronization problem, the first synchronization signal is ignored and thereby the first cardiac cycle is ignored for purposes of delivering a treatment energy signal to the patient. In an alternative embodiment, more than one synchronization signal (e.g., three synchronization signals) can be ignored before the treatment energy signal is delivered again.

Referring back to step 36, if the synchronization module determines that the synchronization problem indicator is low, it means that synchronization is being maintained and step 40 is executed. In step 40, the synchronization module in the control device 1 waits for a predetermined time period (e.g., 50 milliseconds) after the synchronization signal has been received (e.g., starting from the leading edge to logic high) and sends a signal to the energy delivery device 5 to apply the treatment energy signal (see exemplary pulse 92 within the blanking period 96 in FIG. 6). In the embodiment shown, the treatment energy signal is a single IRE pulse of 100 microseconds although a set of pulses can be applied so long as they are not applied during the T-wave phase. Waiting for 50 milliseconds ensures that the treatment energy is applied at an optimal time (e.g., during the refractory period).

Once the synchronization module sends the instruction to apply the treatment energy signal, no more treatment signals are allowed within the remaining blanking period. If a new synchronization signal is received within that same blanking period, it will be rejected as being erroneous and the current blanking period will be dynamically adjusted by another 500 milliseconds from the time the new synchronization signal is received. During the extended blanking period, no new treatment energy signal is allowed to be delivered as will be explained below.

If in step 30, the synchronization module determines that the synchronization signal was received within the current blanking period, this is indicative of cardiac rhythm irregularity and the blanking period will be extended in step 50. See exemplary blanking period in FIG. 10 where the original blanking period 144 has been overlapped with a new blanking period 146 to extend the blanking period in which no new treatment signal can be delivered until the end of the blanking period 146. In step 52, synchronization condition indicator is set to high to indicate that too many synchronization signals are being received. As discussed above, this may indicate a rhythm problem, noise, a loose pad or wire, or ECG double counting. Once step 52 is executed, the synchronization module returns to step 26 where it waits for a new synchronization signal.

In the case of tachycardia, the heart rate by definition is over 120 beats per minute. If the 500 ms blanking period is used, this will cause the blanking period to be dynamically adjusted indefinitely. So, a shorter blanking period should be used.

Figure 3B:
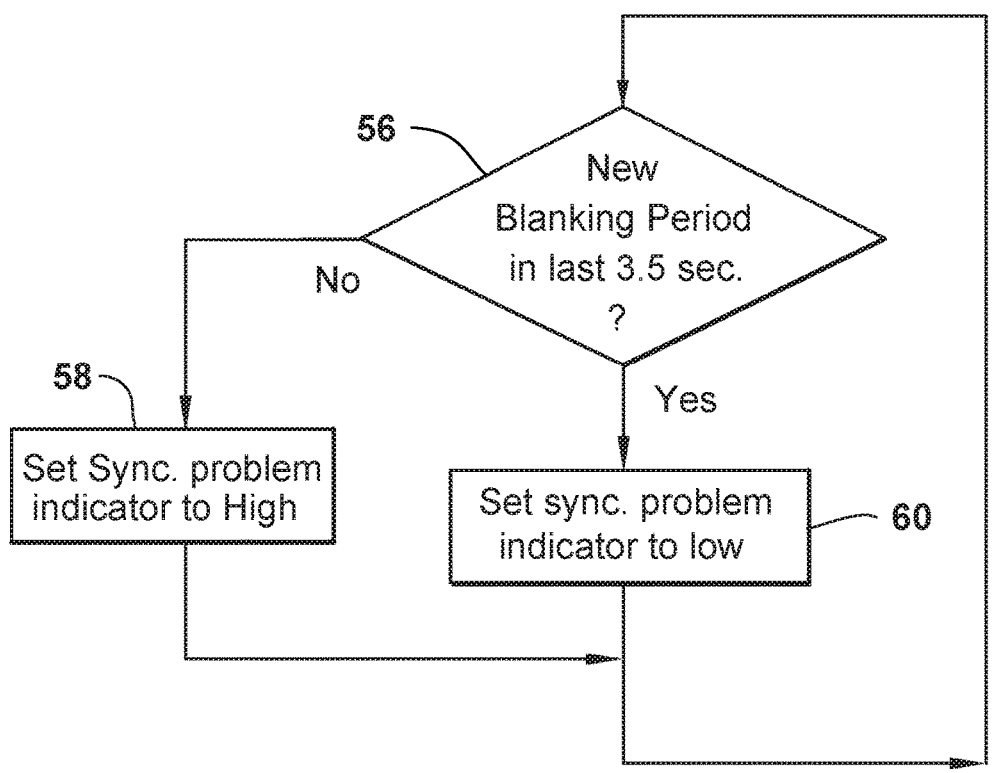

FIG. 3B illustrates a flowchart of a set of steps that are executed by the synchronization module independently of those in FIG. 3A to determine whether the synchronization signal is erroneous. In other words, the steps of FIG. 3A and FIG. 3B are executed concurrently within the synchronization module of the control device 1. In step 56, the synchronization module continuously determines whether a new blanking period has begun within the last 3.5 seconds (the new blanking period is started in step 34 of FIG. 3A). If so, the synchronization problem indicator is set to low in step 60. However if there has been no new blanking period within the last 3.5 seconds, the synchronization problem indicator is set to high. This may mean either that no synchronization signals are being received or that too many are being received to continuously extend the current blanking period (see continuously extending blanking period E in FIG. 10, for example). In that case, the synchronization module sets the synchronization problem indicator to high in step 58 to indicate that the synchronization signal is received in error. After executing either step 58 or step 60, the synchronization module returns to step 56 to check for the new blanking window in order to constantly update the synchronization problem indicator.

Although the control device 1 has been described with reference to an R-wave, it can also use other phases of the cardiac cycle such as the T-wave such that the control device prevents the firing of a treatment energy signal to the patient during the T-wave phase. In that case, the cardiac device 23 will generate a synchronization signal that indicates that a T-wave of a cardiac cycle has been started and the same steps can be performed to dynamically adjust the blanking period, except that no treatment energy will be applied during the T-wave phase. Alternately, the control device can be adapted to prevent the delivery of a treatment signal for a fixed period of time after every occurrence of the synchronization signal indicating that a T-wave phase has been started.

FIGS. 4A-4C depict an ECG waveform for a healthy adult. FIG. 4A shows a normal waveform for approximately 6 heartbeats. FIG. 4B shows a single normal cardiac ECG reading. Specifically shown are the P, Q, R, S, and T portions of the cardiac cycle. The P-wave 68 indicates atrial depolarization that leads to contraction. The QRS complex 70 shows ventricular depolarization that leads to contraction. The T-wave indicates ventricular repolarization 72. Indicated for completeness are the QT interval 74, PR segment 76 and the ST segment 78. FIG. 5C shows normal ECG segment for a healthy adult. The P-wave 68 is generally 80-100 ms, the QRS complex 70 is approximately 60-100 ms, and the QT interval 74 is 200-400 ms.

FIG. 5 shows a waveform of the ECG in relation to when energy for treatment should be released. This shows the preferred 80 (e.g., refractory period) and possible 86 points of the cardiac cycle to release energy for treatments, along with a time where energy should not be released 82 (T-wave portion), and a time where energy release could cause pacing 84. Energy release at 80 will not affect the cardiac rhythm due to the status of depolarization. Energy release at 86 also can be used for release of energy in treatment though through that range some depolarization is occurring. Energy release at 84 could affect heart rate and rhythm and can be used by experts in very specific cases to advance treatment of patients. Energy release at 82 could cause cardiac rhythm irregularities.

FIG. 6 shows a waveform (A) of a normal cardiac rhythm and how the IRE pulse is released in accordance with a certain portion of that cardiac rhythm. Typically the IRE therapy is delivered within the refractory period so that the IRE pulse is matching the depolarized state of the heart. In one embodiment, the IRE energy delivery unit has built in blanking periods 96, 98 (in this example each blanking period is 330 ms) activated when it receives a synchronization signal (B) 88 and 90 corresponding to synchronization signals indicating electrocardiogram electrical signals relating to two heartbeats, respectively. Once the IRE pulse (C) is delivered for a particular blanking period (D), additional synchronization signals received during the same blanking period are disregarded. In this case the electrical signals A for two heartbeats are shown as are the released IRE pulses 92, 94 associated with the electrical signals relating to those two heartbeats.

Figure 7:
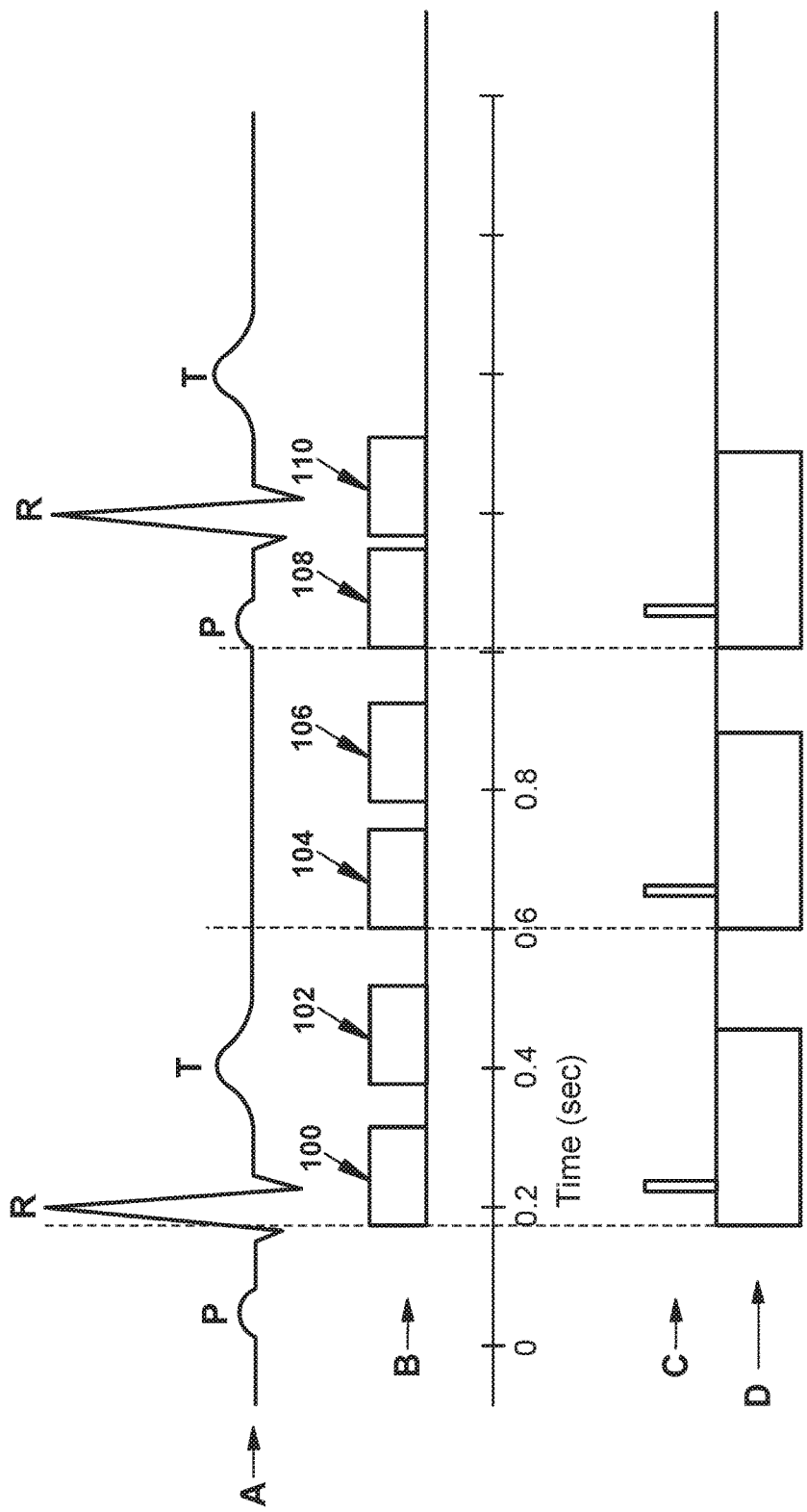
FIG. 7 shows a waveform including a depiction of IRE treatment for a normal QRS rhythm in a noisy environment where the synchronization signal indicates more than 1 R-wave.

FIG. 7 shows a waveform including a depiction of IRE treatment for a normal QRS rhythm in a noisy environment where the synchronization signal (such as from an Accusync device sending a signal or trigger) indicates more than 1 R-wave within a single cardiac cycle. The six synchronization signals are shown as 100, 102, 104, 106, 108, and 110 respectively. There is a need in the art for devices that will monitor and react to conditions such as this, beyond just a blanking period. For systems that have a set blanking period and are not reactive, what will happen in a situation such as this is the following: signal 100 will lead to a proper IRE energy pulse and the second synchronization signal 102 (since the leading edge is in the blanking period) will be ignored, and signal 104 will lead to an IRE energy pulse that is released at the wrong time. Signal 106 will be ignored by the system (as it is in a blanking period), signal 108 will cause an IRE pulse release at the wrong time, and signal 110 will be ignored (since it is in the blanking period). With systems that are improperly activated in a noisy environment, incorrect signals for pulse release can lead to more than 180 IRE energy pulses per minute that are not synchronized with the R-wave.

Figure 8:
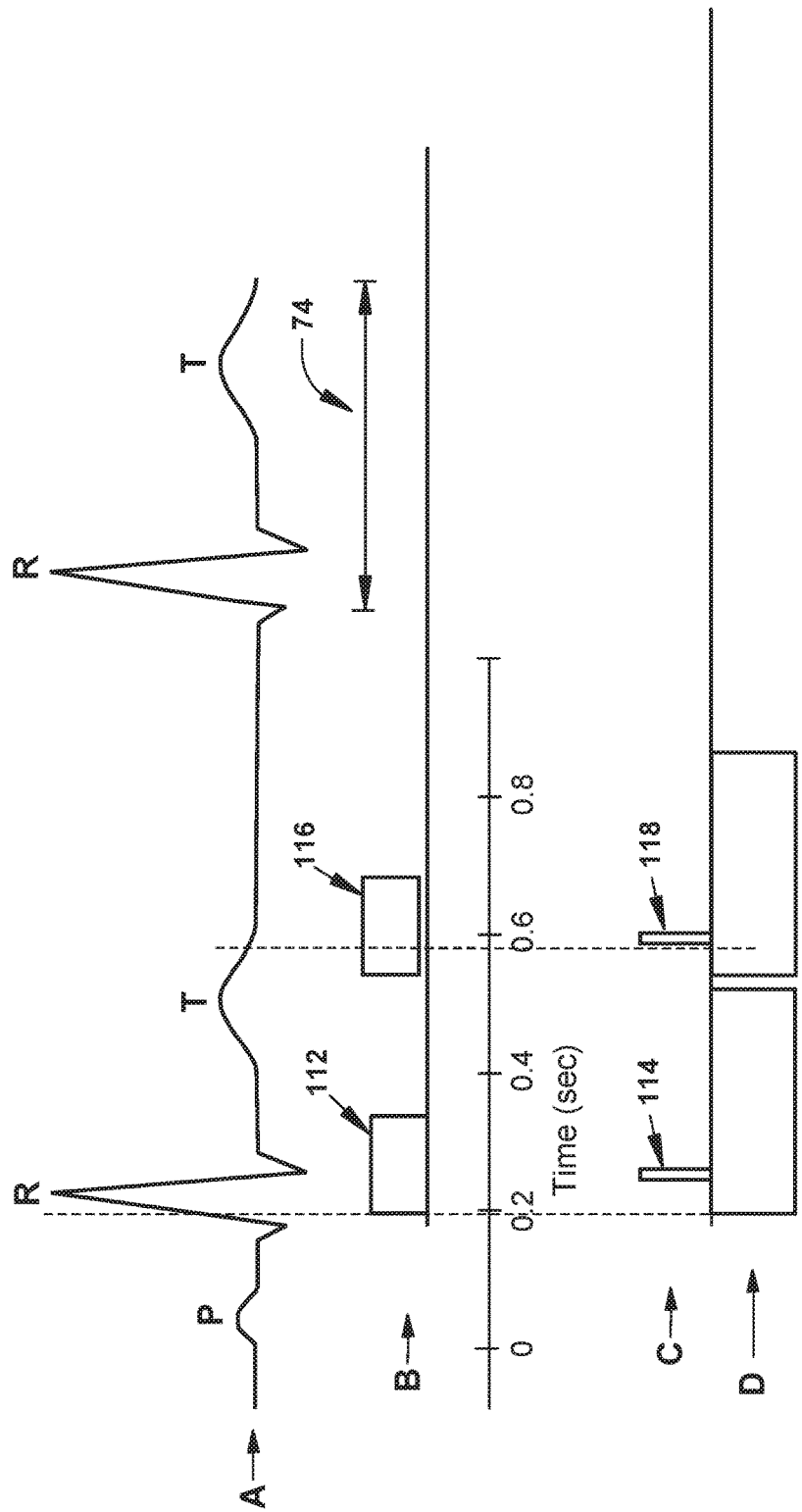
FIG. 8 shows a waveform including a depiction of synchronization signaling when the QRS segment is at the long range of normal.

FIG. 8 shows a waveform including a depiction of synchronization signaling when the QRS segment 70 is at the long range of normal. A QT 74 interval of 400 ms is at the long limit of normal. For systems that have a set blanking period and are not reactive, what will happen in a situation such as this is the following: shown in FIG. 8 is a synchronization signal at the proper time 112 and the proper IRE energy pulse release 114, and a second signal 116 that comes at the incorrect time. Incorrect signals can cause unsynchronized IRE energy pulses, such as after the second synchronization signal 116 that leads to an IRE energy pulse release 118 on the T-wave. An IRE pulse at this time can lead to at least one abnormal cardiac contraction. In one example, if the time from one R wave to another R wave is 1000 milliseconds, then there is 2% chance that the IRE energy pulse would be delivered during the T-wave (since the vulnerable T wave portion would be 20 milliseconds and the released pulse would have a 20/1000 or 2% chance of being delivered at that incorrect time).

Figure 9:
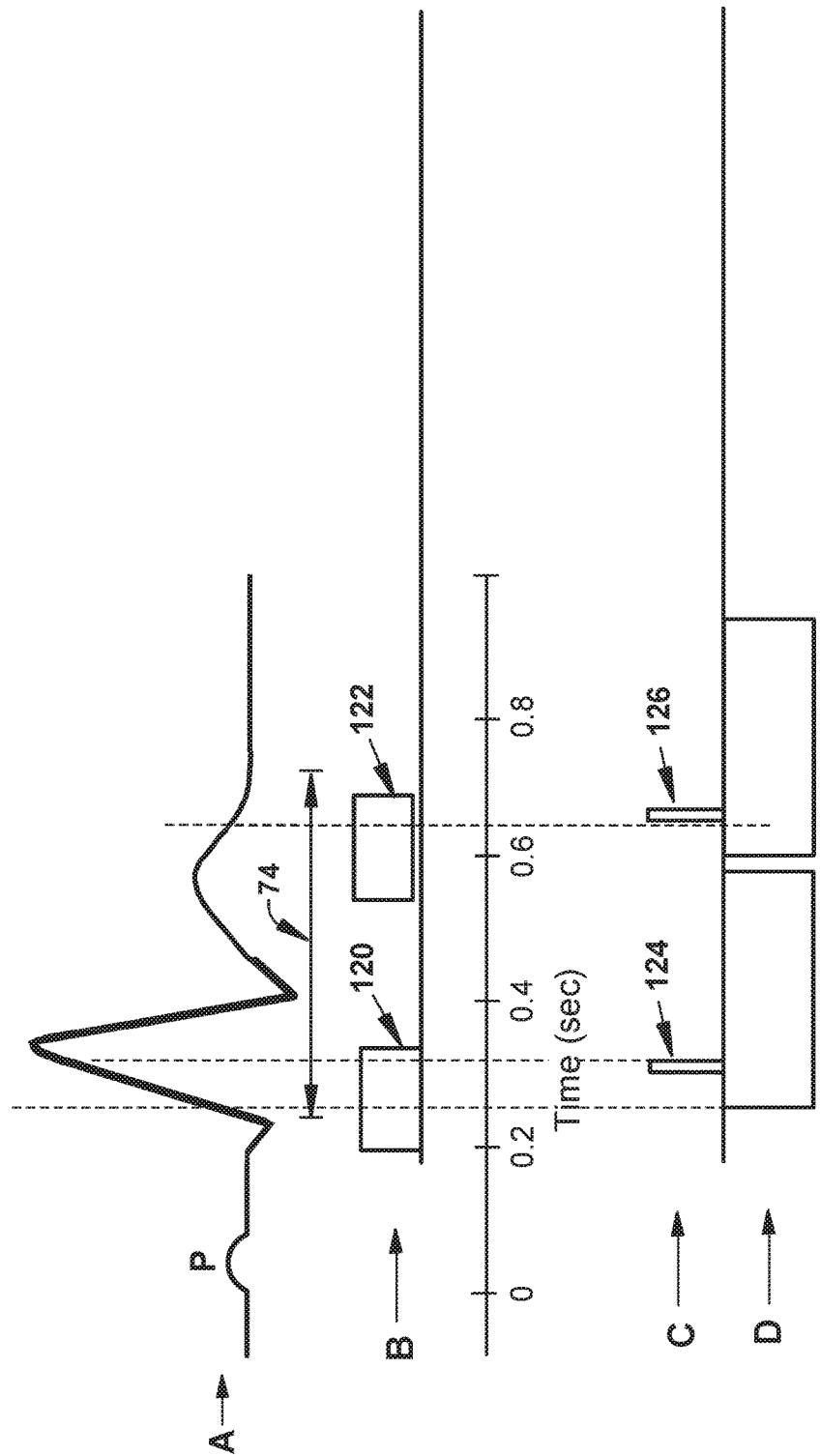
FIG. 9 shows a waveform including a depiction of synchronization signaling when there are ventricular conduction problems such as an abnormally long QRS segment.

FIG. 9 shows a waveform including a depiction of synchronization signaling when there are ventricular conduction problems such as an abnormally long QRS segment. Shown in FIG. 9 are: the QT segment 74, two synchronization signals 120 and 122, and two corresponding IRE energy pulses (124, 126). For systems that have a set blanking period and are not reactive, what will happen in a situation such as this is the following: In this case the QT segment 74 is longer than normal. The first synchronization signal 120 leads to a proper IRE energy pulse release 124. The second synchronization signal comes during the T wave at an improper time and in this example leads to an improper IRE energy pulse release 126. More generally, a QT interval of 500 milliseconds would be an example of the QT segment indicated in FIG. 7. This can occur with Left Bundle Branch blocks or in cases of Dilated Cardiomyopathy. The situation is similar to when the QT interval is 400 milliseconds except that the window where an IRE energy pulse can be released during a T wave becomes greater (such as 120 milliseconds). In an example case random noise could have a 120/1000 or 12% chance of causing an IRE energy pulse release during a T wave. A properly synchronized IRE pulse will land on the QRS complex and can create an abnormal contraction with reduced or with no cardiac output. In general, patients with a history of structural heart disease are at a significantly higher risk for reentrant ventricular tachyarrythmias than the general population. In such cases IRE energy pulse releases during the T wave would be likely to lead to a sustained dangerous cardiac arrhythmia. In current embodiments of the described invention herein, the IRE pulse delivery computer is coupled to computer databases and patient databases so that records and archives can be reviewed (by the IRE pulse delivery computer or a computer or one coupled to it) to obtain and analyze an individual patient's history and likelihoods as well as a population's history and likelihoods. The computer can also be coupled to computers and databases for retrieval and analysis of statistics and medical therapies and recommendations.

Figure 10:
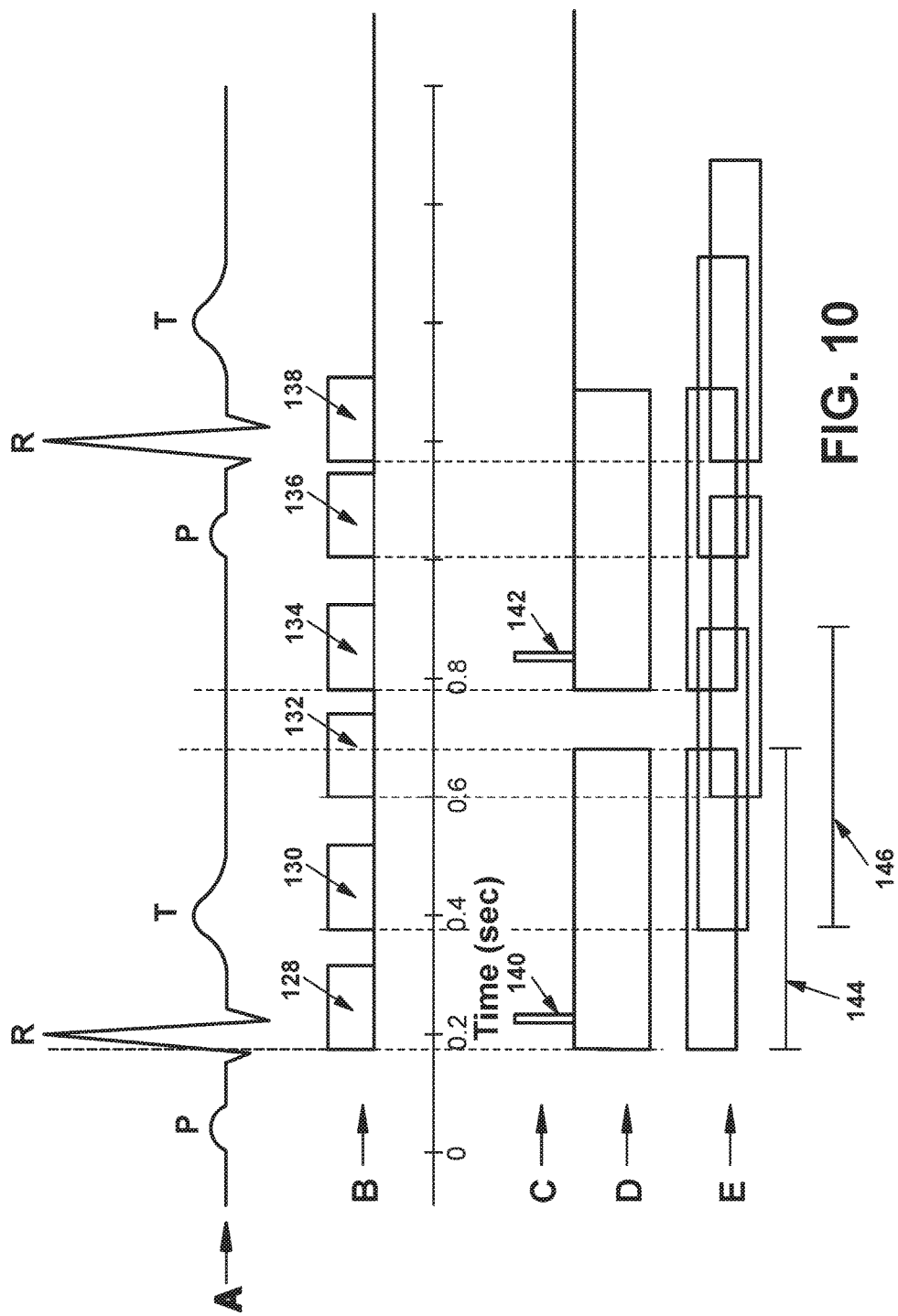
FIG. 10 shows a waveform including a depiction of synchronization signaling where there is a normal QRS segment in a noisy environment.

FIG. 10 shows a waveform including a depiction of synchronization signaling where there is a normal QRS segment in a noisy environment. FIG. 10 shows an advantage of the current invention, which prevents unsafe IRE energy pulse release by providing for the recognition of pulses that occur within a given blanking period and allows for a retriggering of the ongoing blanking period. In other words, if a synchronization signal is received during a blanking period, then in recognition of the fact this is indicative of a dysrhythmia, then the blanking period will be extended so as to account for this disruption. More specifically, FIG. 10 shows six synchronization signals 128, 130, 132, 134, 136, and 138. In a situation where a set blanking period has been put in place, this will lead to two IRE energy pulse releases (140 and 142), however as in this example, the release of the second IRE pulse can be at an undesirable time that can adversely affect cardiac function. One advantage of the current invention is that a blanking period can be extended when synchronization signals are received during the blanking period. In other words if there was a 500 millisecond blanking period starting at time zero, and a signal was received at 250 milliseconds, then at that 250 millisecond point, the blanking period would be extended an additional 500 milliseconds (for a total of 750 milliseconds from time zero). Using this system, then the 6 synchronization signals in FIGS. 9, 128, 130, 132, 134, 136, and 138 would only lead to the first and proper IRE energy pulse release. FIG. 10 shows a normal blanking period 144, and an overlayed, extended blanking period 146.

Figure 11A:
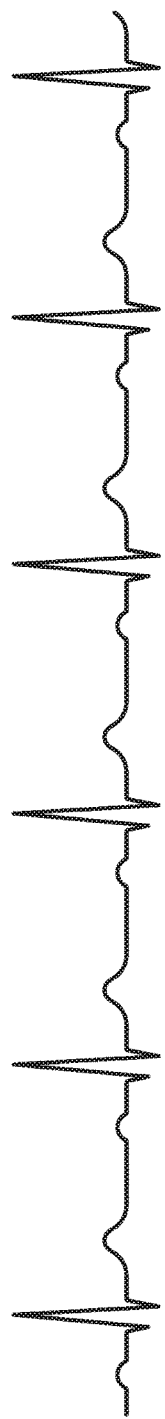
FIGS. 11A, 11B, and 11C show an electrocardiogram waveform of a normal sinus rhythm and of IRE energy pulse release as associated with arrhythmias.
Figure 11B:
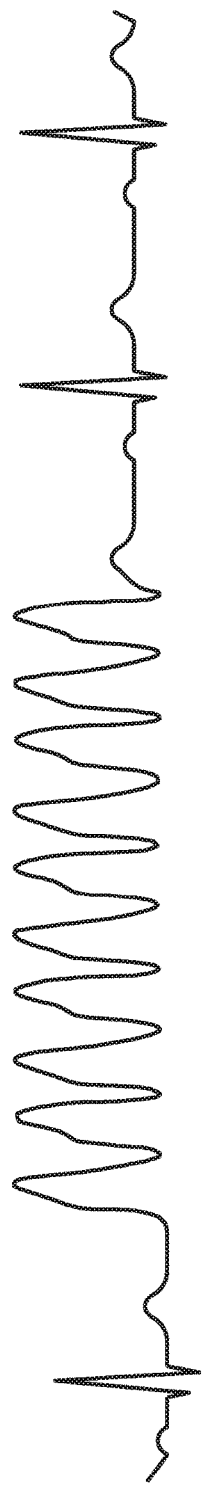
Figure 11C:
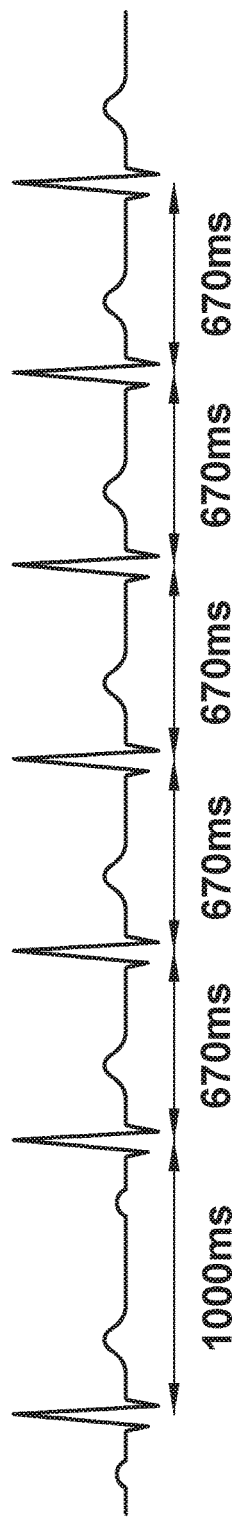

FIG. 11 shows an electrocardiogram waveform of a normal sinus rhythm and of IRE energy pulse release as associated with arrhythmias. FIG. 11 shows an example of the current invention where if necessary, IRE release can affect the sinus rhythm (in situations where electrocardiogram synchronization is not available). More specifically, FIG. 11A shows a normal sinus rhythm (NSR). In comparison, FIG. 11B shows a situation where there is transient arrhythmia (ventricular flutter that can be 240 beats per minute, where cardiac output drops or goes to zero and sustained tachyarrythmia is possible). Tachyarrythmia can occur spontaneously and could potentially occur if IRE pulses were delivered at inappropriate times and therefore affected cardiac depolarization. By contrast, FIG. 11C shows a situation where the heart rhythm has been affected by energy release, as energy release for electroporation can be used to pace the heart. In various embodiments energy release is performed as all or part of a patient treatment where the patient may have an irregular or normal cardiac rhythm, and in those embodiments, treatment indicates an action to benefit the patient condition.

Figure 12A:
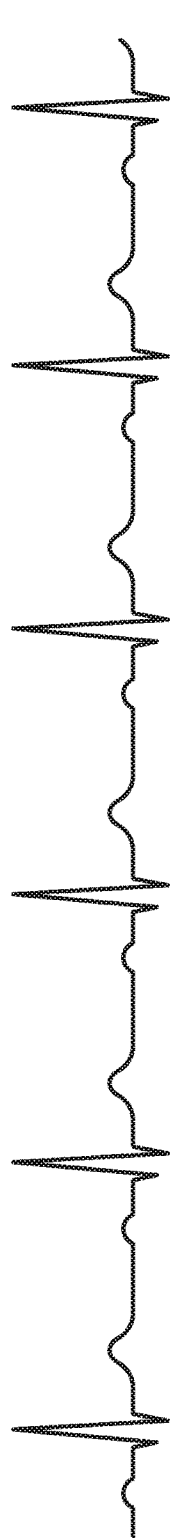
FIGS. 12A-B show a waveform outline of a normal sinus rhythm and a cardiac arrhythmia known as bradycardia.
Figure 12B:
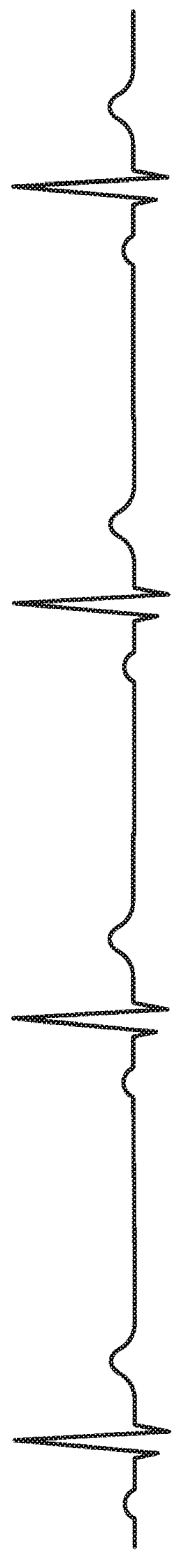
Figure 13A:
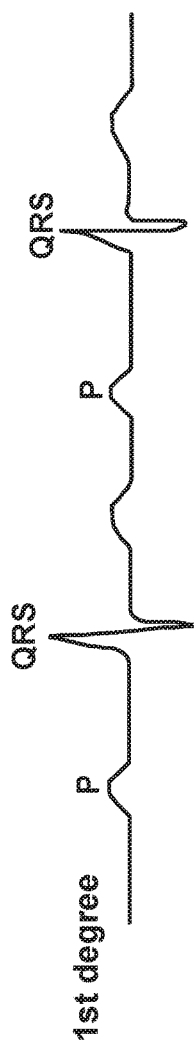
FIGS. 13A, 13B, and 13C show waveforms of problematic, first, second, and third degree conditions of bradycardia.
Figure 13B:
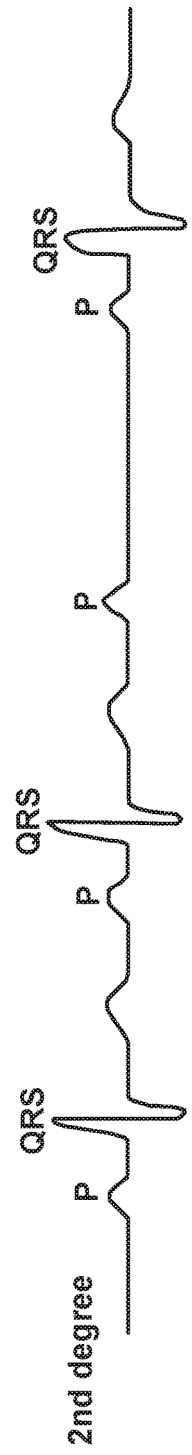
Figure 13C:
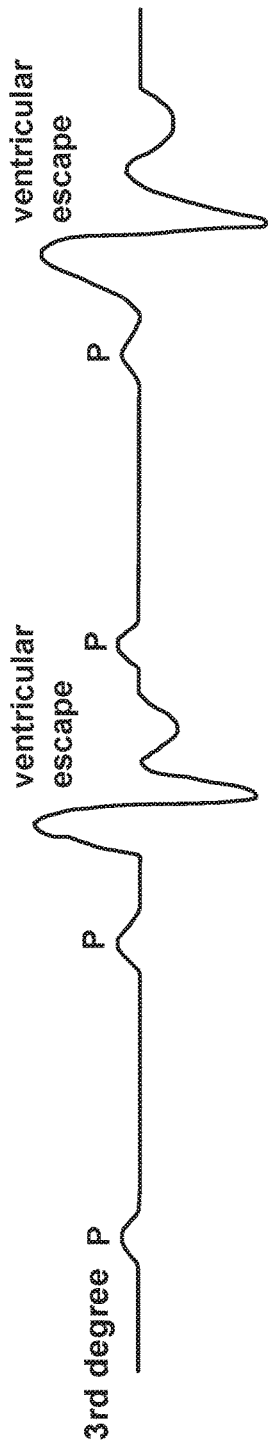
Figure 14:
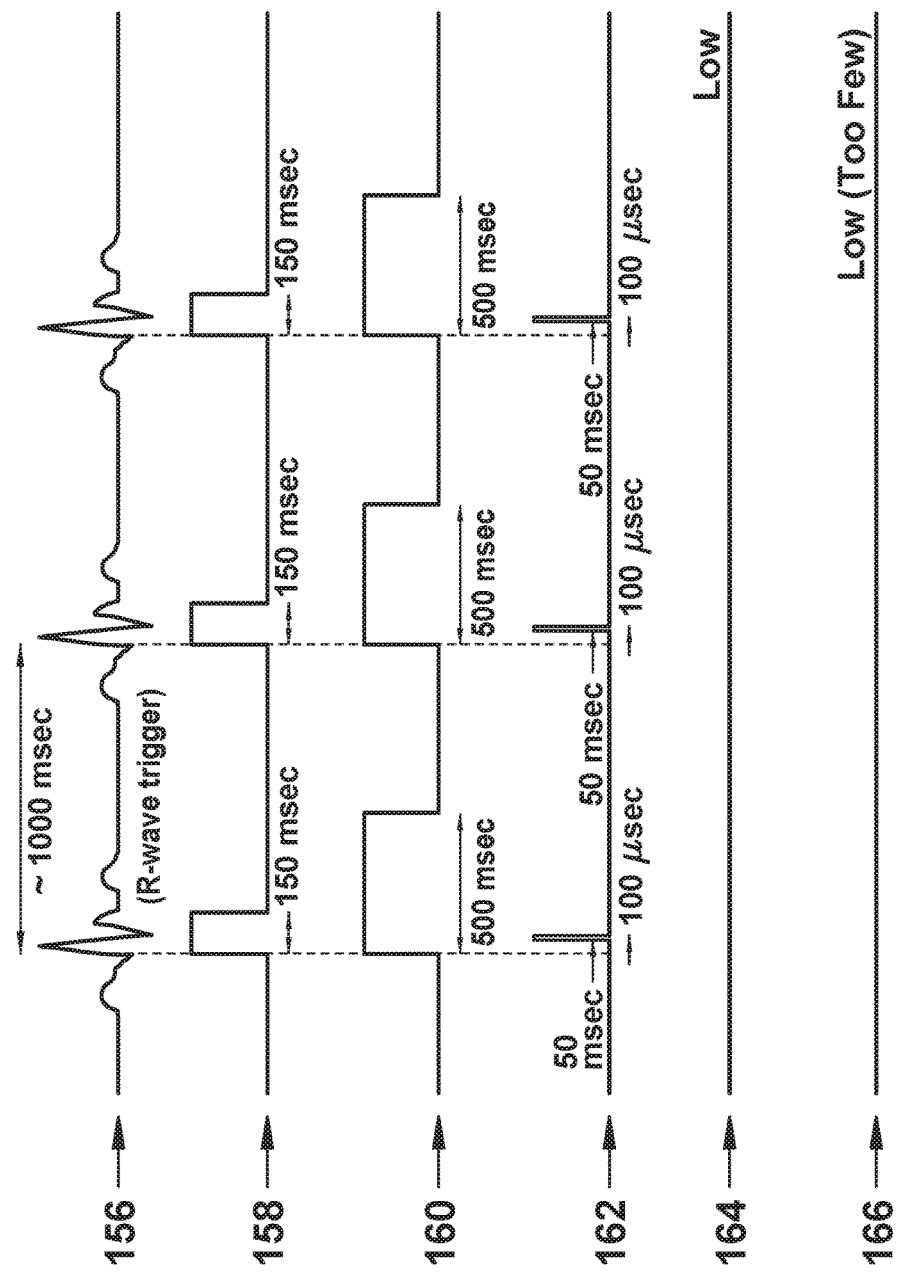
FIG. 14 shows waveforms that indicate a potential display within an embodiment of the current invention showing a cardiac rhythm, output from a synchronization device, output showing blanking, the IRE energy pulse release, and an output showing a synchronization problem and synchronization condition.

FIGS. 12 and 14 show waveforms that outline a cardiac arrhythmia known as bradycardia that is to be accounted for in the IRE energy pulses system. Specifically FIG. 12A shows the normal sinus rhythm, and FIG. 12B shows a slower heart rate (bradycardia). There is a long duration between the P waves. Patients can normally be treated in normal IRE synchronization mode. FIG. 13 shows problematic bradycardias where these arrhythmias indicate underlying conduction problems. FIG. 13A shows an example of first degree bradycardia, FIG. 13B shows second degree bradycardia, and FIG. 13C shows third degree bradycardia. Ideal IRE energy release systems will recognize changes in the cycle such that IRE pulses are not released at an inappropriate portion of the cycle.

FIG. 14 shows waveforms that indicate a potential display within an embodiment of the current invention showing a cardiac rhythm 156, output from a energy delivery control device 158 (shown as Accusync in this example), output showing blanking 160, the IRE energy pulse release 162 (shown here as treatment), and an output showing a synchronization problem indicator 164 and synchronization condition indicator 166. Each of 164 and 166 represent indicators or internal mechanisms to demonstrate on the graphic user interface that there has been a change or is an aberrant cardiac rhythm in which to take into account for optimal IRE energy pulse release. These indicators are part of the energy delivery control device demonstrated in FIGS. 4-6. In certain embodiments of the energy delivery control device, the Accusync synchronization device is used, synchronization output is generated on every R-wave, the patient has a normal rhythm morphology, the RT interval is less than 500 ms, and the anesthetized heart rate is 50-70 beats per minute.

Table 1, below, shows a chart indicating embodiments indicating multiple modes of IRE energy pulse delivery contemplated for the current invention.

TABLE 1

| Delivery Mode | Description | When Used |
| --- | --- | --- |
| Mode 1 - ECG Synchronized (Default Mode) | 3rd Party synchronization (cardiac) device generates a sync signal on patient R-wave. Energy delivery device delivers IRE pulse 50 ms after sync signal. | Thoracic or abdominal locations (liver, lung, pancreas). |
| Mode 2 - Low rate, Not ECG Synchronized | Energy delivery device delivers 90 IRE pulses in trains of 10 pulses each. 670 ms between (90 pulses/min) and 3.5 seconds between trains | Only if sync problems prevent treatment. |
| Mode 3 - High rate, Not ECG Synchronized | Energy delivery device delivers 90 IRE pulses in trains of 10 pulses each. 250 ms between pulses (240 pulses/min) and 3.5 seconds between trains. | Prostate. (Plus other distal locations in the future). |

Mode 1 is an electrocardiogram synchronized mode where a third party synchronization device generates a synchronization signal on the patient R-wave. An IRE energy delivery device delivers an IRE pulse 50 ms after the synchronization signal. Mode 1 can be used for many IRE energy pulse release locations, including but not limited to thoracic, abdominal, liver, lung, and pancreas. Table 1 also shows a second mode; mode 2 involves a low cardiac rate, not electrocardiogram synchronized. An IRE energy pulse device delivers pulses. In certain embodiments the release involves 90 pulses in trains of 10 pulses each (where a train is consecutive pulses released), and where there are 670 ms between pulses, and 3.5 seconds between trains of pulses. Mode 2 can be used if synchronization problems would otherwise prevent treatment. Table 1 also shows a third mode; mode 3 involves a high cardiac rate, not electrocardiogram synchronized. An IRE energy pulse release device delivers pulses. In certain embodiments 90 pulses are released in trains of 10 pulses each, with 250 ms between pulses (240 pulses per minute) and 3.5 seconds between trains. Mode 3 can be used, among other options, to treat prostate and areas and regions adjacent to the prostate. In various embodiments the moment for energy release for ablation is determined from the peak of the R-wave, and in other embodiments it is determined from part of the slope of the R-wave prior to or following the peak of the R-wave. In various embodiments the moment for energy release is determined in relation to when the R-wave has reached ⅓ of its ultimate peak height on the ECG reading, and on other embodiments, the energy release is determined in relation to when the R-wave has reached ⅔ of its ultimate peak height on the ECG reading. The readings and calculations (involving determinations for energy release) and visual display of results can be performed in real-time.

FIGS. 15-19 indicate waveforms of timing diagrams indicating how the synchronization condition and synchronization problem indicators change in relation to various cardiac rhythms. In certain example embodiments of the invention, the terms Cardiac 156, Accusync 158, Blanking 160, Treatment 162, Sync Problem 164, Sync Condition 166, and Sync Status 168 refer to the following: 1) Cardiac: the 3 lead surface electrocardiogram seen by a synchronization device, 2) Accusync: a synchronization device that is a 5 Volt transistor transistor synchronization (TTL)—signal output by Accusync that is 150 ms long, 3) Blanking is an internal 500 ms blanking period programmed into software associated with the Energy delivery device 5 (such as NanoKnife IRE System from AngioDynamics of Latham, N.Y.)—where the blanking starts with each synchronization signal and during an active blanking period synchronization signals do not trigger an IRE pulse, 4) Treatment: Output from the energy delivery device, 5) Sync Problem—(Synchronization problem)—an internal indicator in the stored in the memory of the control device 1 that is normally in the low state, and that switches to the high state if no IRE pulse is delivered in 3.5 seconds—the synchronization module communicates changes in the Sync Problem state to the graphic user interface—and if the Sync Problem is high for 12 seconds the software aborts treatment, 6) Sync Condition—(Synchronization Condition) is an internal indicator in the memory of the control device 1 that is normally in the low state and that switches to high when the control device 1 receives a synchronization signal during a blanking period—and switches back to low when a synchronization signal is received outside of a blanking period, 7) Sync Status is a message displayed on the NanoKnife (or other energy delivery device) display by the graphic interface user depending on the state of the Sync Problem indicator and the Sync Condition indicator.

Figure 15:
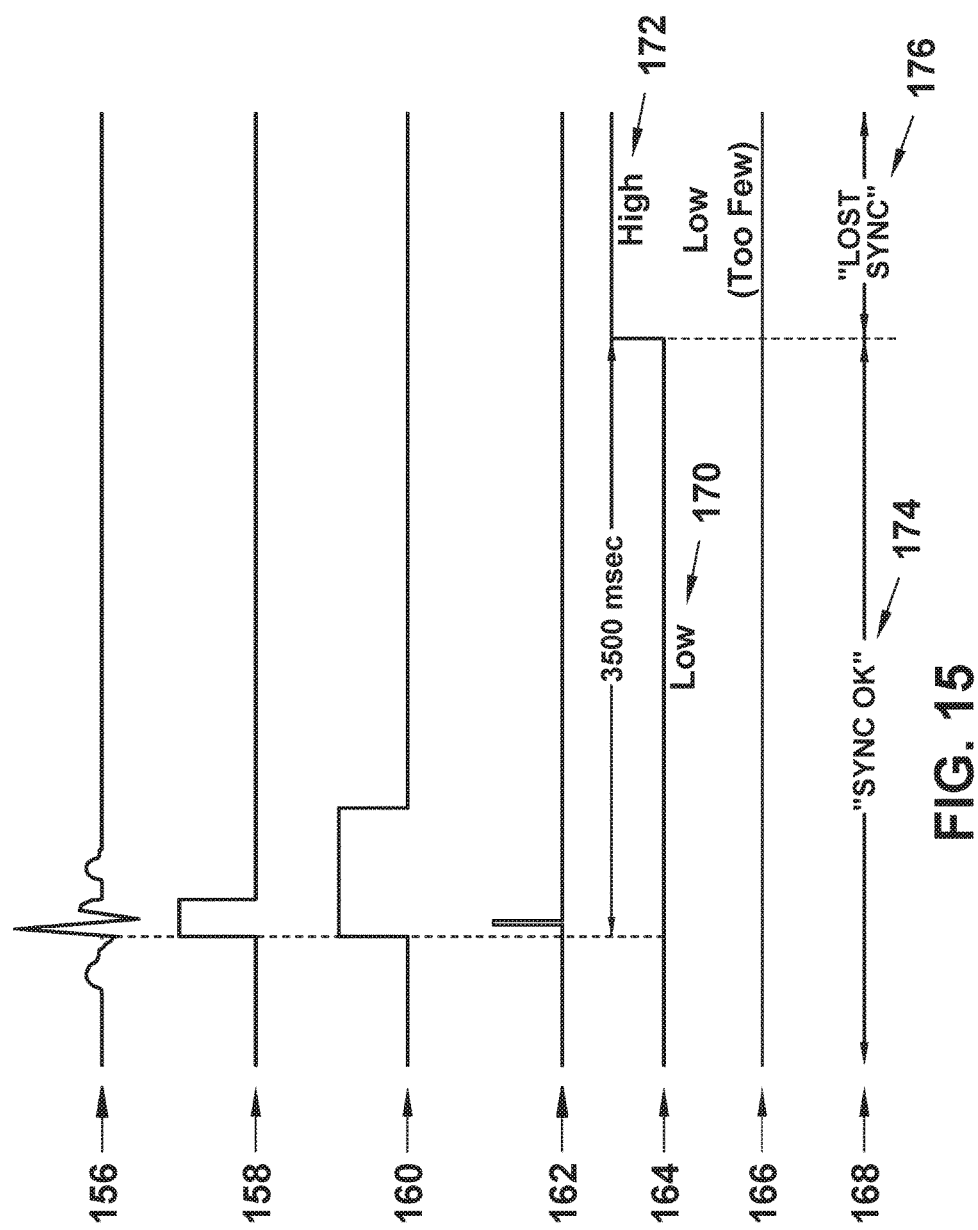
FIG. 15 indicates waveforms of timing diagrams indicating how the synchronization condition and synchronization problem indicators change in relation to various cardiac rhythms, most specifically referring to a lost synchronization condition.

Referring now to FIG. 15, this shows waveforms for Cardiac 156, Accusync 158, Blanking 160, Treatment 162, Sync Problem 164, and Sync Condition 166, and Sync Status 168. FIG. 15 shows an example of lost synchronization. There is a single electrical signal for a cardiac rhythm shown, and then it stops. There is one Accusync signal released 158 and one IRE energy pulse release 162. The Sync Problem level starts at a low setting 170, and after 3.5 seconds the Sync Problem setting changes to high 172. The Sync Status 168 changes from "Sync OK" 174 to "Sync Lost" 176 or otherwise indicates the change graphically.

Figure 16:
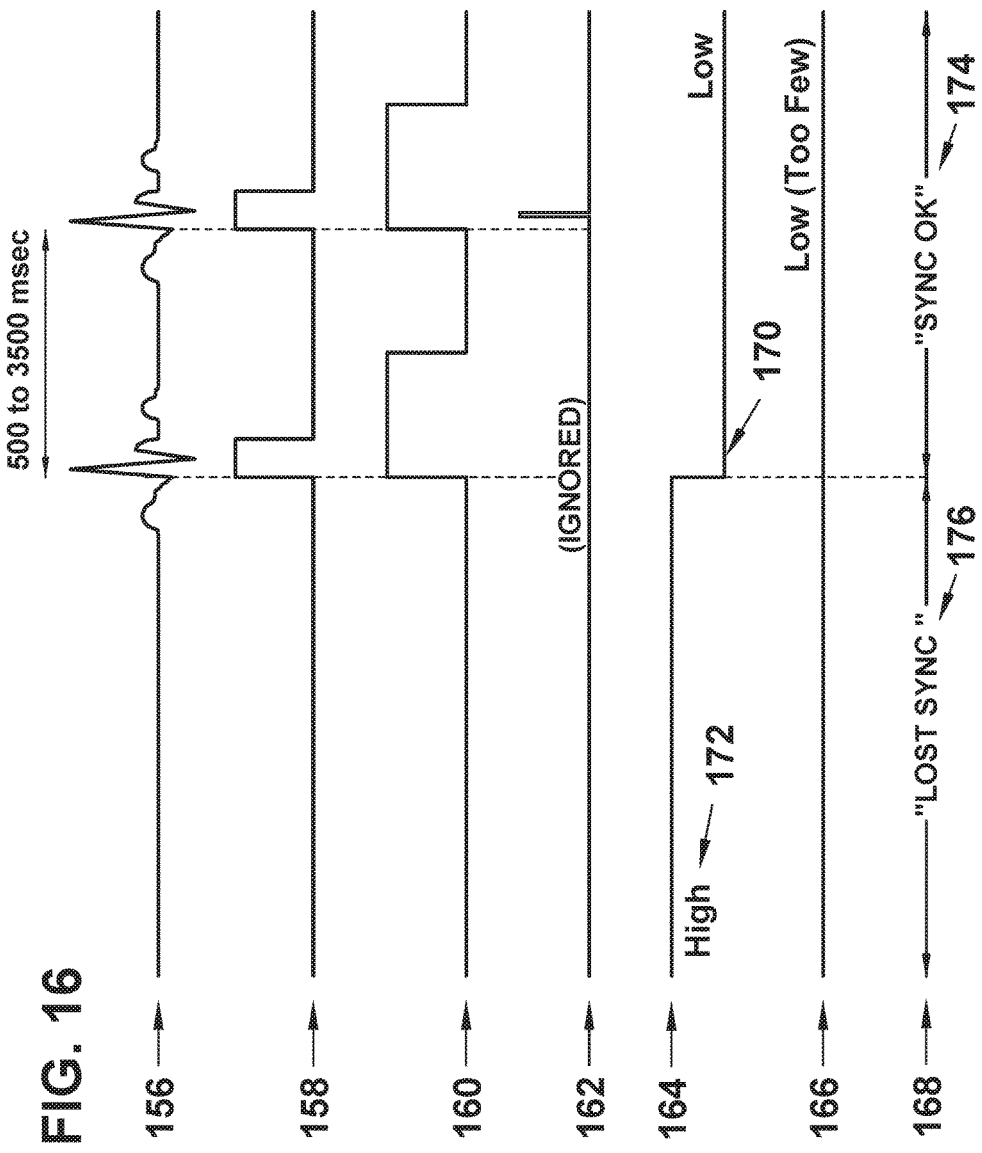
FIG. 16 indicates waveforms of timing diagrams indicating how the synchronization condition and synchronization problem indicators change in relation to various cardiac rhythms, most specifically referring to recovery from a lost synchronization condition.

FIG. 16 shows waveforms for a lost synchronization recovery. A Cardiac signal returns 156, and the Sync Problem level falls from high 172 to low 170. The Sync Status output changes back from "Sync Lost" 176 to "Sync OK" 174.

Figure 17:
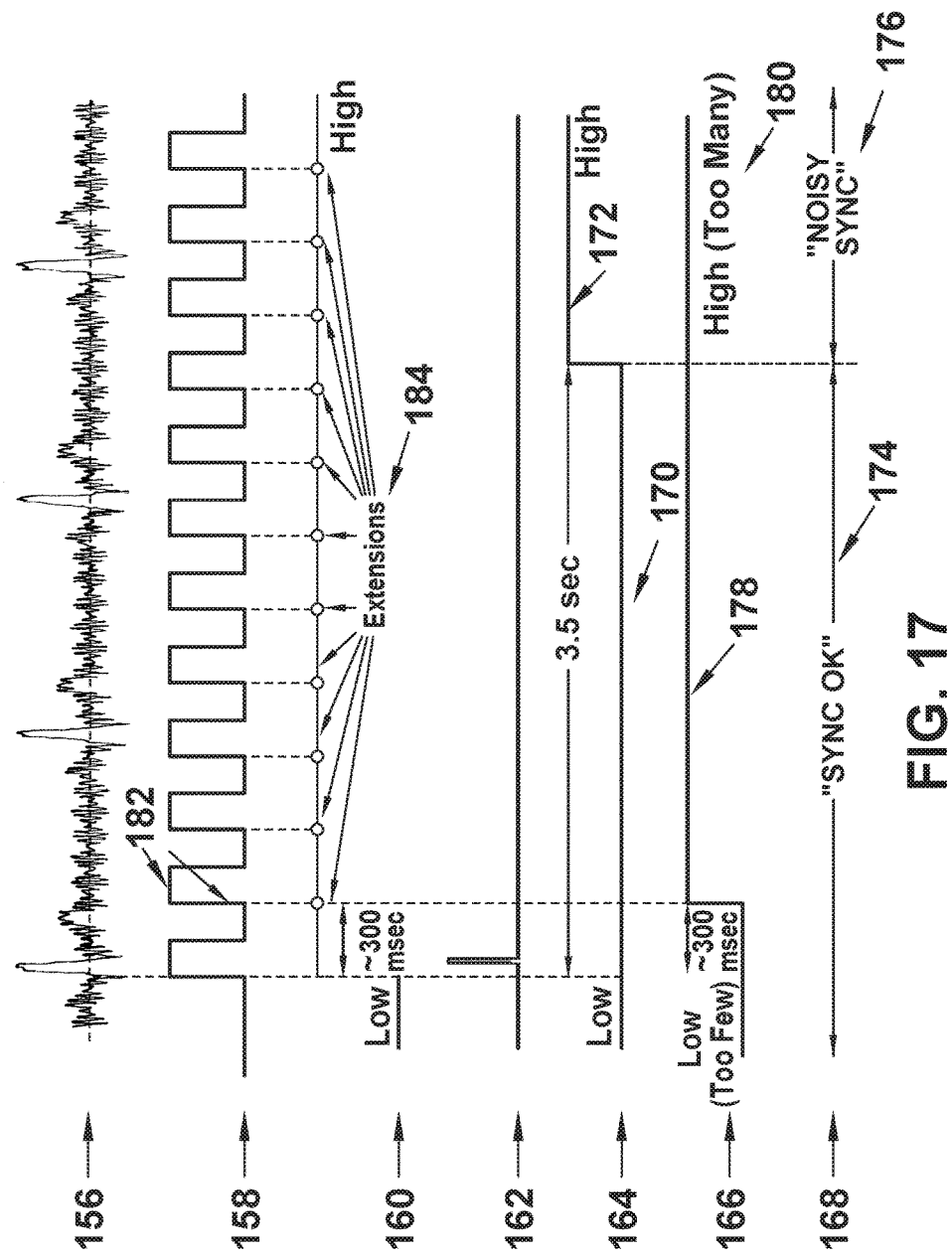
FIG. 17 indicates waveforms of timing diagrams indicating how the synchronization condition and synchronization problem indicators change in relation to various cardiac rhythms, most specifically referring to output change in a noisy signal condition.

FIG. 17 shows waveforms for how the Sync Problem 164, Sync Condition 166, and Sync Status 168 outputs change in a noisy signal condition. First, a lot of noise can be seen in the Cardiac electrical rhythm 156. The synchronization signal (Accusync, 158) output shows that synchronization pulses are received within the blanking periods 182. There are Blanking periods 160 and extensions in response 184. One IRE pulse (treatment, 162) is delivered and that is all. The Sync Problem 164 level changes from low 170 to high 172 after 3.5 seconds. The Sync Condition 166 level changes from low 178 to high 180. The Sync Status 168 output changes from "Sync OK" 174 to "Noisy Sync" 176 or some equivalent graphical display.

Figure 18:
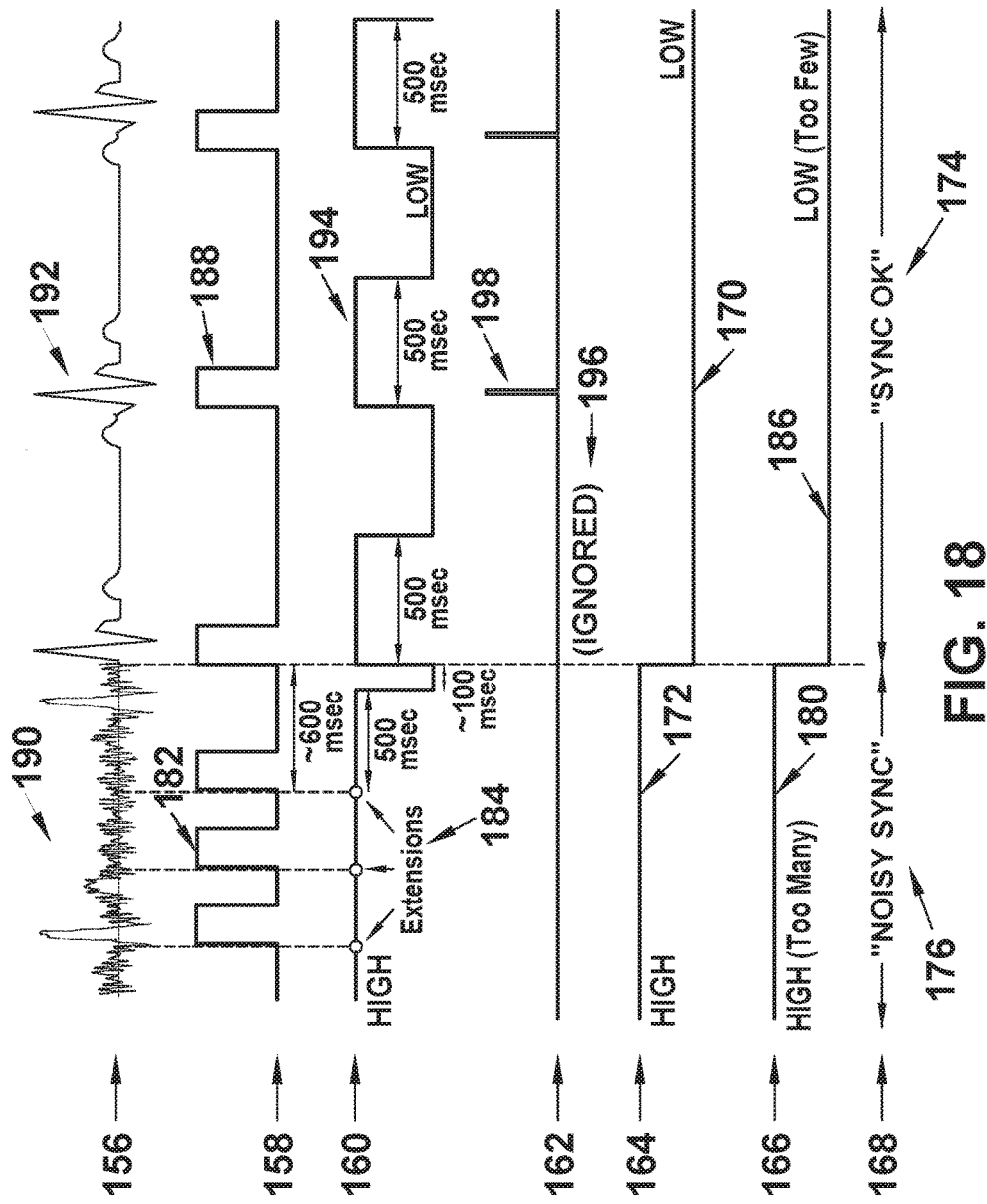
FIG. 18 indicates waveforms of timing diagrams indicating how the synchronization condition and synchronization problem indicators change in relation to various cardiac rhythms, most specifically referring to output for recovery from a noisy signal condition.

FIG. 18 shows waveforms for recovery from a noisy signal condition. The Cardiac electrical signal output 156 changes from noisy (aberrant) 190 to normal 192. The Accusync output 158 changes from signals within the blanking range 182 to the normal signals 188 as the cardiac rhythm returns to normal. The Blanking periods 160 that were being extended 184 return to the normal 500 ms blanking times with gaps between 194. The IRE energy pulse release (treatment, 162) returns 198, with the first Accusync signal being ignored 196 (and with there being a release on the second normal Accusync signal). The Sync Problem indicator 164 changes from high 172 to low 170 as the normal cardiac rhythm returns. The Sync Condition indicator 166 changes from high 180 to low 186, and the Sync Status 168 output moves from "Noisy Sync" 176 to "Sync OK" 174.

Figure 19:
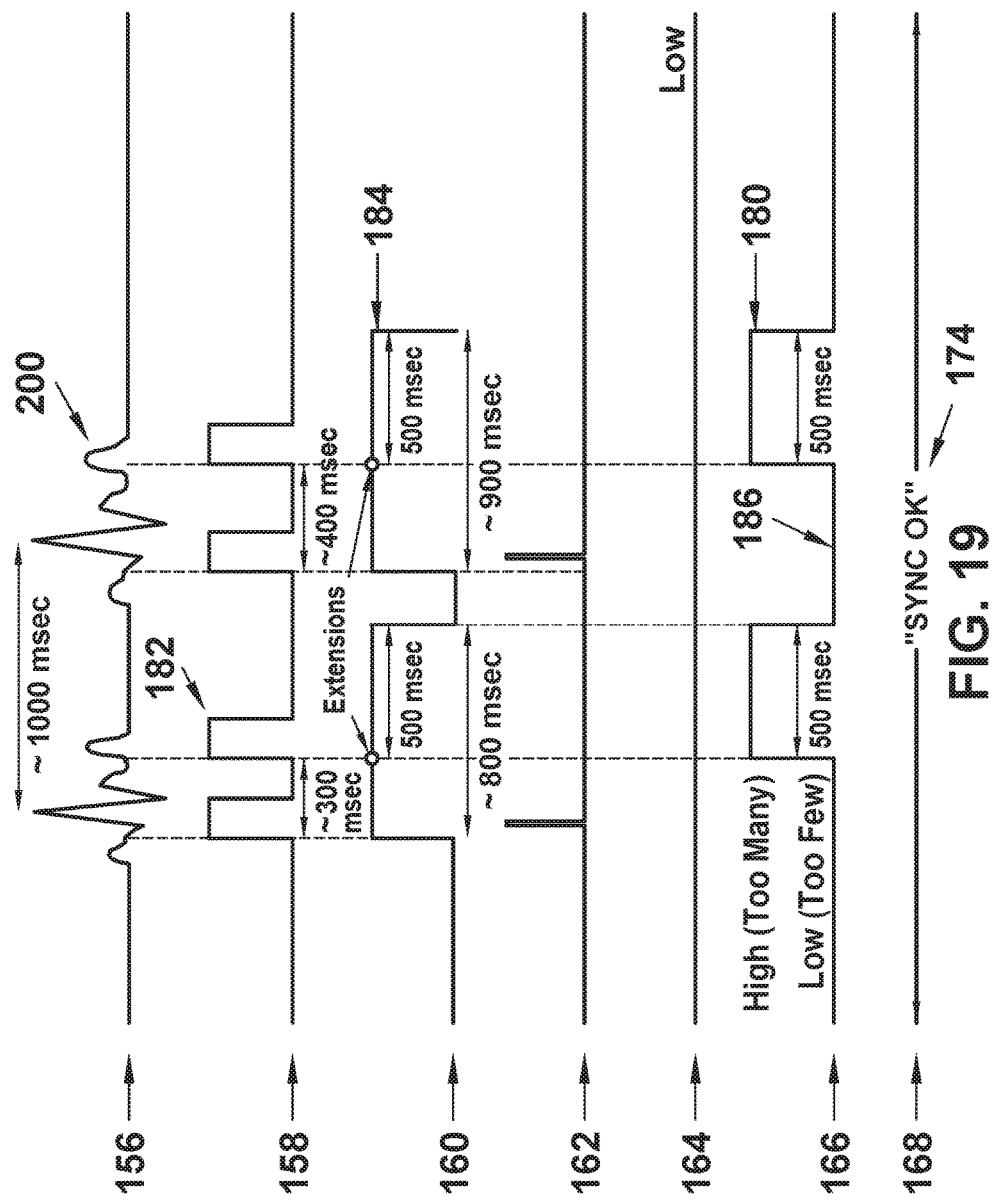
FIG. 19 indicates waveforms for timing diagrams indicating how the synchronization condition and synchronization problem indicators change in relation to various cardiac rhythms, most specifically referring to output for double counting of the T wave.

FIG. 19 indicates waveforms for output that shows a situation where due to a T wave abnormality, the T wave is counted twice by the synchronization signaling device (Accusync) so a second synchronization signal is indicated. The Cardiac electrical signal output 156 shows an aberration near the T wave 200. As a result, there is a second synchronization signal (Accusync output 158) within the blanking period 182, and the blanking period (line 160) is extended 184 to account for this. The Sync Condition indicator (line 166) moves from low 186 to high 180 and then returns to low once the normal synchronization signal is received. In this example treatment can continue and the Sync Status 168 remains as "Sync OK" 174 throughout. Treatment line 162 is shown for completeness.

FIGS. 20A-B and 21A-B indicate waveforms that show two examples of modes of IRE delivery discussed in Table 1. FIG. 20 shows mode 2 (FIG. 20B is an expanded view of part of FIG. 20A) and FIG. 21 shows mode 3 (FIG. 21B is an expanded view of FIG. 21A). In FIG. 20, there are 90 pulses of 100 microseconds (100 microseconds for each pulse 206), 670 milliseconds between pulses 204, with a delivery rate of 90 pulses per minute, delivered in trains of 10 pulses 202, with 3500 milliseconds between trains. In FIG. 21 showing mode 3, there are 90 pulses of 100 microseconds (100 microseconds for each pulse 206), 250 milliseconds between pulses 208, with a delivery rate of 240 pulses per minute, delivered in trains of 10 pulses 202, with 3500 milliseconds between trains.

While the embodiments shown use IRE pulses as treatment energy signals, persons of ordinary skill in the art will appreciate that the present invention can work with any other treatment energy signals and may work particularly well for treatment signals that may potentially affect the heart beat or signal processing in a cardiac device that generates synchronization signals.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

What is claimed:

1. A method for synchronizing application of treatment signals with a cardiac rhythm, comprising:
   placing a medical treatment device at a target site within a patient
   starting a system for synchronizing treatment signals with the cardiac rhythm, the system comprising:
   a memory that receives and stores a first synchronization signal indicating that a predetermined phase of the cardiac rhythm of a patient has started; and
   a synchronization module coupled to the memory to receive the first synchronization signal, a blanking period beginning after receiving the first synchronization signal, the synchronization module operable to automatically extend the blanking period the moment a second synchronization signal is received during the blanking period without stopping the blanking period to prevent the treatment signal from being applied to the patient during the blanking period; and
   delivering a treatment signal when the blanking period has concluded.

2. The method of claim 1, wherein the synchronization module dynamically adjusts the blanking period during which an application of the treatment signal to the patient by the medical treatment device is prevented.

3. The method of claim 2, wherein the synchronization module is operable to dynamically extend the blanking period when a new synchronization signal is received before the blanking period expires.

4. The method of claim 2, wherein the synchronization module is operable to start a new blanking period when a subsequent synchronization signal is received by the memory after the blanking period.

5. The method of claim 1, wherein the synchronization module, after receiving the first synchronization signal, controls the medical treatment device to apply the treatment signal after waiting a predetermined time period from the receipt of the first synchronization signal.

6. The method of claim 5, wherein the synchronization module controls the medical treatment device to apply at least one IRE pulse as the treatment signal.

7. The method of claim 1, wherein the memory receives the first synchronization signal for each occurrence of an R-wave from a cardiac device.

\* \* \* \* \*